US006116235A

United States Patent [19]
Walters et al.

[11] Patent Number: 6,116,235
[45] Date of Patent: Sep. 12, 2000

[54] VAPOR RETENTION ASSEMBLY

[75] Inventors: Mark A. Walters; Ernest G. Schutt, both of San Diego, Calif.; John K. Hoffman, Fall City; Mark H. Wyzgala, Bellevue, both of Wash.; W. Dean Kirkland, El Cajon, Calif.

[73] Assignee: Alliance Pharmaceutical Corp.

[21] Appl. No.: 08/884,598

[22] Filed: Jun. 27, 1997

Related U.S. Application Data

[62] Division of application No. 08/654,551, May 29, 1996, Pat. No. 5,829,428.

[51] Int. Cl.[7] .................... A61M 15/00

[52] U.S. Cl. .................... 128/200.24; 128/205.27; 128/205.29; 128/206.16; 128/205.12; 128/913

[58] Field of Search .................... 128/205.27, 205.29, 128/206.16, 205.12, 913, 200.24

[56] References Cited

U.S. PATENT DOCUMENTS

| | | | |
|---|---|---|---|
| 4,516,573 | 5/1985 | Gedeon | 128/201.13 |
| 5,035,236 | 7/1991 | Kanegaonkar | 128/201.13 |
| 5,195,527 | 3/1993 | Hicks | 128/205.12 |
| 5,437,272 | 8/1995 | Fuhrman | 128/203.12 |
| 5,460,172 | 10/1995 | Eckerbom et al. | 128/201.13 |
| 5,490,498 | 2/1996 | Faithfull et al. | 128/203.12 |

FOREIGN PATENT DOCUMENTS

| | | |
|---|---|---|
| 0 081 655 | 6/1983 | European Pat. Off. . |
| 0 265 163 | 4/1988 | European Pat. Off. . |
| 44 38 216 A1 | 10/1994 | Germany . |
| 2 267 840 | 12/1993 | United Kingdom . |
| WO 88/07876 | 10/1988 | WIPO . |
| WO 93/09833 | 5/1993 | WIPO . |
| WO 94/08652 | 4/1994 | WIPO . |
| WO 96/35911 | 11/1996 | WIPO . |

OTHER PUBLICATIONS

Branson, et al. "Humidification in the Intensive Care Unit: Prospective Study of a New Protocol Utilizing Heated Humidification and a Hygroscopic Condenser Humidifer" Chest 104: 1800–1805 (1993).

Hedley, et al. "A Comparison of the Filtration Properties of Heat and Moisture Exchangers" Anaesthesia 47: 414–420 (1992).

Rosi, et al. "Increasing Serum Lithium Concentrations in Patients Ventilated with Hygroscopic Lithium Coated HMEs" 14th International Symposium on Intensive Care and Emergency Medicine 5(2 Supp): Mar. (1994).

*Primary Examiner*—Aaron J. Lewis
*Attorney, Agent, or Firm*—Knobbe, Martens, Olson & Bear LLP

[57] ABSTRACT

Methods and apparatus for the conservation of respiratory promoters following their pulmonary introduction are disclosed. In preferred embodiments the present invention provides methods and apparatus for reducing the loss of respiratory promoter, and particularly fluorochemcials, during medical procedures such as liquid ventilation. The disclosed methods comprise the use of vapor retention assemblies, which may be conventional heat and moisture exchangers, to passively retain the respiratory promoter and return it to the lungs in subsequent breaths. Novel vapor retention assemblies comprising fluorophilic exchange elements are also disclosed.

15 Claims, 8 Drawing Sheets

VAPOR RETENTION ASSEMBLY

This application is a division of application Ser. No. 08/654,551, filed May 29, 1996 now U.S. Pat. No. 5,829,428.

FIELD OF THE INVENTION

In a broad aspect the present invention relates to methods and apparatus for the conservation of respiratory promoters following their pulmonary introduction. More particularly, the present invention relates to reducing the loss of respiratory promoter during medical procedures such as liquid ventilation.

BACKGROUND OF THE INVENTION

Respiration involves the introduction of fresh gases, especially oxygen, to the lung during inspiration and the removal of waste gases, particularly carbon dioxide, during expiration. In healthy individuals respiration is normally effected by spontaneous ventilation or breathing which results in the introduction of necessary gases. Unfortunately, a number of physiological and pathological processes may compromise normal pulmonary function leading to the inhibition of effective respiration or total respiratory failure. In such cases respiratory therapy, often involving artificial ventilation to some degree, is indicated. For example, respiratory therapy is often indicated for patients undergoing surgery or those suffering disorders and diseases of the pulmonary air passages. In particular, patients suffering from lung contusion, diver's lung, post-traumatic respiratory distress, post-surgical atelectasis, irritant injuries, septic shock, multiple organ failure, Mendelssohn's disease, obstructive lung disease, pneumonia, pulmonary edema or any other condition resulting in lung surfactant deficiency or respiratory distress are strong candidates for respiratory therapy. Typically, such respiratory therapy involves the use of mechanical ventilators.

Mechanical ventilators are clinical devices that effect ventilation or, in other words, cause air (or gas) flow in the lungs. More specifically, such devices typically force air into the lungs during the inspiration phase of the breathing cycle but allow a return to ambient pressure during spontaneous exhalation. The forced influx of fresh air by mechanical ventilation facilitates the pulmonary mediated processes that comprise respiration in mammals. One of these processes, removal of waste gases, is a primary mechanism by which carbon dioxide is excreted from the body. In normal gas mediated carbon dioxide removal, fresh air is brought into contact with the alveoli (alveolar ventilation) thereby promoting gas exchange wherein carbon dioxide passes from the body and is exhaled during the expiration phase of the breathing cycle. The other essential bioprocess, oxygenation, comprises the absorption of oxygen into the blood from the lungs. It is primarily a function of a mechanism whereby the partial pressure of oxygen ($PO_2$) in pulmonary capillary blood equilibrates with the partial pressure of oxygen in inflated alveoli. The oxygen gradient between alveolus and capillary favors transfer of oxygen into blood because the repeated influx of fresh oxygen through ventilation (spontaneous or assisted) maintains alveolar $PO_2$ at higher levels than capillary $PO_2$. Modern mechanical ventilators are designed to provide ventilation by regulating tidal volume (breath), flow rate, delivery profile and respiratory flow thereby controlling carbon dioxide excretion. Because they can also regulate airway pressure and the concentration of inspired oxygen they offer control over oxygenation as well.

At least twenty makes and models of mechanical ventilators are used in North America today. Almost all the ventilators used in operating rooms, recovery rooms and intensive care units are volume-controlled ventilators. With a device of this type the operator may set tidal volume, respiratory rate, and inspiratory rate, allowing the ventilator to deliver a set volume of gas regardless of the airway pressure. Such devices usually have a pressure cutoff to prevent damage to the lungs. In contrast, pressure-controlled ventilators are standard in neonatal intensive care, in chronic ventilator management, and during patient transport. Pressure-controlled ventilators typically allow the operator to select the respiratory rate, the inspiratory gas flow and the peak airway pressure. The ventilator then delivers inspired gas, while monitoring the tidal volume, until the desired pressure is reached. Unfortunately, in both types of commercially available ventilators the expired gases, including any bioactive agents introduced during inspiration or exhaled pathogenic material, are typically released into the environment during use.

Another complication associated with conventional mechanical ventilation arises due to the composition of the delivered gases. Normally, inspired gas is conditioned by the upper respiratory tract and the trachea to ensure that it is saturated with water vapor prior to entering the delicate environment of the lower respiratory tract. In particular, the inspired gas is heated by convection in the upper respiratory tract while, at the same time, water vapor is added by evaporation. That is, the upper part of the airway acts as a thermoregulator adding heat and moisture to the inspired gas and extracting it from the exhaled gas. Unfortunately, mechanical ventilation often interferes with this natural physiological process by introducing cool unhumidified gas. This leads to dehydration of the respiratory tract potentially causing (1) impairment of ciliary activity; (2) impairment of mucus movement; (3) inflammatory changes and necrosis of the pulmonary epithelium; (4) bacterial infiltration; (5) atelectasis; and (6) pneumonia.

Due to the possible consequences, steps are typically taken to prevent the dehydration of the pulmonary surfaces during mechanical ventilation. Perhaps the most common step is actively pretreating the gas through the addition of water vapor and heat prior to pulmonary introduction. Another method of conditioning the gas as it is introduced into the lungs is through the use of passive heat and moisture exchangers. Heat and moisture exchange devices, or artificial noses, are used in medical applications to take up heat and moisture from a patient's exhaled breath and transfer it to inhaled gas. Specifically, they are designed to retain a portion of the expired moisture and heat and return it to the patient's respiratory tract during inspiration. Although they are produced using a number of different configurations, the present generation of exchange devices typically employs a hygroscopic element to absorb heat and moisture during expiration and release it as dry cool air from the ventilator passes over the element during inspiration.

The oldest and least efficient these devices is the heat and moisture exchanger (or HME) which consists of an aluminum insert and, optionally, a fibrous element. Because aluminum rapidly changes temperatures, moisture is deposited between the layers of the insert during exhalation. The retained heat and moisture is then returned, at least in part, during inhalation. Another type of exchange device is the heat and moisture exchanging filter (HMEF) which contains a hydrophobic fibrous insert that traps heat and adsorbs moisture on the patient side of the filter. Perhaps the most common type of exchange devices today are the hygroscopic condenser humidifiers (HGH) and hygroscopic condenser humidifying filters (HGHF) that use absorption to exchange heat and moisture. These devices comprise and element, typically paper, that is treated with lithium chloride or calcium chloride to increase the thermodynamic efficiency of the exchange. In the HGHF a bacterial filter is juxtaposed between the insert and the source of gas. While the use of artificial noses slightly increases flow resistance in the respiratory circuit, such devices have been found to provide safe and effective humidification for most patients.

Recently alternative techniques, particularly liquid ventilation, have been developed to obviate at least some of the complications associated with mechanical gas ventilation. In contrast to standard mechanical ventilation, liquid ventilation involves introducing an oxygenated liquid medium into the pulmonary air passages for the purposes of waste gas exchange and oxygenation. Essentially, there are two separate techniques for performing liquid ventilation, total liquid ventilation and partial liquid ventilation. Total liquid ventilation or "TLV" is the pulmonary introduction of warmed, extracorporeally oxygenated liquid respiratory promoter (typically fluorochemicals) at a volume greater than the functional residual capacity of the subject. The subject is then connected to a liquid breathing system and tidal liquid volumes are delivered at a frequency depending on respiratory requirements while exhaled liquid is purged of $CO_2$ and oxygenated extracorporeally between the breaths. This often involves the use of specialized fluid handling equipment. Conversely, partial liquid ventilation or "PLV" involves the use of conventional mechanical ventilation in combination with pulmonary administration of a respiratory promoter capable of oxygenation. As with TLV, the respiratory promoter typically comprises fluorochemicals which may be oxygenated prior to introduction. In the instant application the term "liquid ventilation" will be used in a generic sense and shall be defined as the introduction of any amount of respiratory promoter into the lung, including the techniques of both partial liquid ventilation and total liquid ventilation.

Avoiding some of the complications associated with TLV, partial liquid ventilation, as described in Fuhrman, U.S. Pat. No. 5,437,272 and Faithfull et al. U.S. Pat. No. 5,490,498, is a safe and convenient clinical application of liquid breathing using fluorochemicals which are oxygenated in vivo. In PLV a liquid, vaporous or gaseous respiratory promoter (i.e. a fluorochemical) is introduced into the pulmonary air passages at volumes ranging from just enough to interact with a portion of the pulmonary surface all the way up to the functional residual capacity of the subject. Respiratory promoters are any compound that functions, systemically or pulmonarily, to improve gas exchange and respiration efficiency. Respiratory gas exchange is thereafter maintained for the duration of the procedure by continuous positive pressure ventilation using a conventional open-circuit gas ventilator. Like total liquid ventilation, the pulmonary introduction of the respiratory promoter eliminates surface tension due to pulmonary air/fluid interfaces while improving pulmonary function and gas exchange in surfactant deficiency and other disorders of the lung. As PLV does not require continued extracorporeal oxygenation, well established conventional off-the-shelf ventilators may be used to provide the necessary oxygenation and carbon dioxide purging in vivo. Moreover, as it is predominantly gas rather than liquid that moves in tidal fashion with each breath, the airway pressures required for the procedure may be much lower than during TLV. Finally, when the procedure is over the introduced the liquid, gaseous or vaporous respiratory promoter may be allowed to evaporate from the lung rather than being physically removed as in TLV.

As previously indicated, fluorochemicals are the preferred respiratory promoter for both TLV and PLV. Generally, fluorochemicals compatible with liquid ventilation will be clear, odorless, nonflammable, and essentially insoluble in water. Preferred fluorochemicals are denser than water and soft tissue, have a low surface tension and, for the most part, a low viscosity. In particular, many brominated fluorochemicals are known to be safe, biocompatible substances when appropriately used in medical applications. It is additionally known that oxygen, and gases in general, are highly soluble in some fluorochemicals. For example, some fluorochemical liquids may dissolve over twenty times a much oxygen and over thirty times as much carbon dioxide as a comparable amount of water. Oxygenatable fluorochemicals act as a solvent for oxygen. They dissolve oxygen at higher tensions and release this oxygen as the partial pressure decreases. Carbon dioxide behaves in a similar manner.

In addition to carrying gases and removing waste products, respiratory promoters such as fluorochemicals may be used as pulmonary drug delivery vehicles, either in conjunction with liquid ventilation or as independent therapy. For example, aerosol delivery systems may rely on a mixture of therapeutically active agents with one or more respiratory promoters to increase dispersion, efficacy and stability of the bioactive agent. Moreover, fluorochemicals have been shown to have pulmonary and systemic antiinflammatory effects. Accordingly, despite relatively high costs, it is desirable to employ fluorochemicals as the respiratory promoter of choice in current liquid ventilation procedures and pulmonary drug delivery.

While liquid ventilation is a significant improvement over conventional ventilation, the escape of fluorochemicals into the environment in the form of vapors gases or aerosols, compromises the effectiveness of PLV therapy. That is, many of the most desirable fluorochemicals are volatile to some extent and naturally evaporate over the course of the treatment. During normal liquid fluorochemical ventilation procedures the generation and release of such vapor may be significant. For example, in current PLV therapy conventional mechanical ventilators release the expired gas, including fluorochemicals, into the environment. In adult PLV treatments evaporative fluorochemical losses may correspond to a significant portion of the material introduced to the lung over the course of the therapy. Of course, if the therapy is to be continued additional respiratory promoter must be added to maintain effective residual volumes. As fluorochemical liquids and other respiratory promoters suitable for liquid ventilation can be relatively expensive, such losses can substantially increase the cost of such treatments. Moreover, the loss of respiratory promoter complicates both dosing regimens and regulation of the current volume of material in the lung.

The problem of fluorochemical loss during liquid ventilation is addressed in co-pending U.S patent application Ser. No. 08/566,023 which is directed to methods and apparatus for closed-circuit ventilation. While the disclosed methods and apparatus are extremely effective at reducing the loss of breathable liquids during liquid ventilation, the equipment necessary to practice the disclosed invention is specialized may not always be available. This is particularly true of situations in less developed countries where the latest medical techniques may not be practiced. Moreover, such equipment can be expensive depending on the configuration of the apparatus and the condition of the patient. Thus, there remains a need by which to retain respiratory promoters and, in particular, breathable liquids during liquid ventilation that is relatively efficient in terms of both cost and ease of use.

Accordingly, it is an object of the present invention to provide simple and cost effective methods of reducing the loss of respiratory promoters, including breathable liquids, during liquid ventilation.

It is another object of the present invention to reduce the loss of respiratory promoters, including breathable liquids, through the use of off-the-shelf components.

It is yet another object of the present invention to provide an apparatus for reducing the loss of a respiratory promoter during liquid ventilation.

It is still another object of the present invention to provide a vapor retention assembly for reducing the loss of pulmonarily introduced fluorochemicals.

SUMMARY OF THE INVENTION

These and other objectives are achieved by the present invention which, in a broad aspect, is directed to methods and apparatus for the retention of respiratory promoters in the lung. In preferred embodiments, the present invention provides methods and devices for use in liquid ventilation procedures to reduce the unintentional loss of valuable materials, including fluorochemicals, into the environment. Among other advantages, the apparatus and methods disclosed herein reduce the cost of such therapy by retaining the administered respiratory promoter, decreasing the interruptions in ventilatory care and reducing the requirement for operator intervention.

The present invention is predicated on the unexpected discovery that a vapor retention assembly (or vapor retainer) could be used to reduce the loss of respiratory promoter from the lung during ventilation procedures. Preferably the respiratory promoter introduced into the lung is a liquid or vapor of a liquid and, in particularly preferred embodiments, a breathing liquid (i.e. a fluorochemical) capable of transporting oxygen. Typically the respiratory promoter is introduced into the pulmonary air passages as a free flowing liquid or as an aerosol or vapor. As used herein, the phrases "vapor retention assembly" or "vapor retainer" are interchangeable and shall be held to mean any apparatus or article of manufacture that reversibly associates with, and subsequently releases, a respiratory promoter. In selected embodiments the vapor retention assembly can be a commercially available heat and moisture exchanger typically used in conventional ventilation procedures. Other embodiments involve the use of novel vapor retention assemblies comprising a fluorophilic exchange element. Both types of vapor retainers have been found to substantially reduce the loss of fluorinated breathing liquid from the lungs.

Accordingly, one aspect of the invention comprises a process for reducing the loss of a respiratory promoter from the pulmonary air passages of a patient wherein the method comprises the steps of:

a. introducing a liquid or vapor respiratory promoter into pulmonary air passages of a respiring patient;

b. connecting an exogenous vapor retention assembly comprising at least one exchange element to said pulmonary air passages so that exhaled gas from the patient and subsequently inhaled breathing gas contact said exchange element;

c. contacting said exchange element with exhaled gas comprising at least a portion of said introduced respiratory promoter;

d. reversibly associating at least a part of the exhaled respiratory promoter with the exchange element; and e. thereafter contacting said exchange element with a breathing gas whereby a portion of the associated respiratory promoter is entrained by the breathing gas and returned to the pulmonary air passages of the patient upon inhalation.

It will be appreciated that the present invention may be used with respiratory promoters, including breathing liquids (i.e. fluorochemicals), bioactive agents and pharmaceutical agents to effect ventilation therapy including, but not limited to, partial liquid ventilation. As used herein the term "ventilation" will be held to mean airflow in the lungs. Accordingly, the term "ventilation therapy" broadly means any procedure, including partial liquid ventilation or the pulmonary administration of any therapeutic or diagnostic agent, that comprises airflow in the lungs. As such, ventilation therapy may be used in connection with the present invention to treat both systemic and pulmonarily localized conditions.

Another major advantage of the present invention is that the disclosed methods and apparatus may optionally be used with conventional mechanical ventilators desirable in extended ventilation therapy. In particularly preferred embodiments, the methods of the present invention are used in conjunction with partial liquid ventilation techniques employing the pulmonary introduction of a breathing liquid in conjunction with a mechanical ventilator. Such partial liquid ventilation techniques may be practiced using novel vapor retainers comprising a fluorophilic exchange element or conventional vapor retention assemblies such as heat and moisture exchangers. Of course it will be appreciated that the methods and apparatus of the present invention are also compatible with patients undergoing spontaneous respiration following the pulmonary introduction of a respiratory promoter. In either case, the rate of respiratory promoter loss from the lungs will be substantially reduced and the therapeutic efficiency of the treatment will be enhanced.

Thus, in another embodiment the present invention provides methods for performing partial liquid ventilation, comprising:

a. introducing a breathing liquid into the pulmonary air passages of a respiring patient, whereby vaporized breathing liquid becomes entrained in gas exhaled by said patient;

b. directing said gas exhaled by said patient through a vapor retainer having affinity for said entrained vapor, such that at least a portion of said vapor becomes retained in said vapor retainer; and then c. directing breathing gas through said vapor retainer and thereafter into said pulmonary air passages of said patient, whereby at least a portion of said retained vapor is carried by said breathing gas back into the pulmonary air passages of the patient.

In accordance with the teachings herein, it will be appreciated that the present invention may be used to treat patients suffering from almost any pulmonary disorder. Particular disorders that are compatible with the disclosed methods and apparatus include, but are not limited to respiratory distress syndrome, lung contusion, chronic lung injury, acute lung injury, diver's lung, post-traumatic respiratory distress, post-surgical atelectasis, irritant injuries, septic shock, multiple organ failure, Mendelssohn's disease, obstructive lung disease, pneumonia and pulmonary edema. Moreover, the invention may be used in conjunction with the pulmonary administration of a bioactive agent associated with a respiratory promoter, particularly a breathing liquid.

It will be further appreciated that the respiratory promoter may be introduced into the pulmonary passages of the patient at any time during the disclosed methods. That is, selected embodiments of the invention comprise introducing the respiratory promoter prior to connecting the vapor retainer while in others the promoter may be introduced after the patient is intubated and undergoing ventilation. In particularly preferred embodiments the patient is initially dosed with an effective amount of respiratory promoter, preferably a fluorochemical liquid or vapor, prior to the initiation of mechanical ventilation. Additional respiratory promoter is then added intermittently to maintain the desired pulmonary volume over the treatment period.

Besides the methods disclosed herein, the present invention also provides novel vapor retention assemblies for use in partial liquid ventilation. These assemblies comprise:

a housing defining a chamber and having a plurality of connecting ports formed therein, said chamber and said connecting ports comprising a gas flow passage through the chamber between the connecting ports, said assembly further comprising a fluorophilic exchange element positioned in said chamber so as to intersect said gas flow passage, whereby the fluorophilic element reversibly associates with a portion of any fluorochemical in expiratory gas passing through the gas flow passage and releases the retained fluorochemical into inspiratory gas passing through the gas flow passage.

With regard to this aspect of the present invention, the fluorophilic exchange element may comprise any material capable of absorbing, adsorbing or otherwise reversibly associating with a fluorochemical vapor upon contacting said vapor. Although any material may be used to provide the desired fluorophilic exchange element, preferred embodiments of the invention incorporate exchange elements comprising silicone, urethane, plastics such as polypropylene, polyethylene or polyesters, composite materials comprising thermoset or thermoplastic resins or any material containing at least one halogenated compound. In particularly preferred embodiments the fluorophilic exchange element comprises a fluorinated compound. Preferred fluorophilic exchange elements have a large surface area and may comprise quilted disks or wafers, scrimmed materials, fluorinated tapes, fibrous constructs, foams or other porous conformations and particulate constructions. Moreover, the fluorophilic exchange elements may be combined with conventional hydrophilic exchange elements to provide vapor retainers that humidify as well as reduce the loss of respiratory promoter. In addition, as the novel vapor retention assemblies of the present invention may be fabricated from reliable, yet cost effective, materials, they may be designed to be disposable thereby reducing operating costs in terms of personnel and maintenance.

Finally, vapor retention assemblies compatible with the present invention may be used to form novel ventilation systems for performing partial liquid ventilation. In particular such systems may comprise:

a patient-connector capable of establishing fluid conducting communication with pulmonary air passages of a patient;

a ventilating circuit sealingly affixed to said patient connector whereby a gas flow path capable of transporting an inspiratory gas into the pulmonary air passages and removing subsequently generated expiratory gases, said ventilating circuit operably associated with a mechanical ventilator;

a vapor retainer in fluid conducting communication with said gas flow path whereby said inspiratory gas and said expiratory gas alternately pass through said vapor retainer; and a liquid or vapor respiratory promoter dispersed in said gas flow path.

Other objects, features and advantages of the present invention will be apparent to those skilled in the art from a consideration of the following detailed description of preferred exemplary embodiments thereof taken in conjunction with the Figures which will first be described briefly.

DETAILED DESCRIPTION OF THE INVENTION

Figure 1:
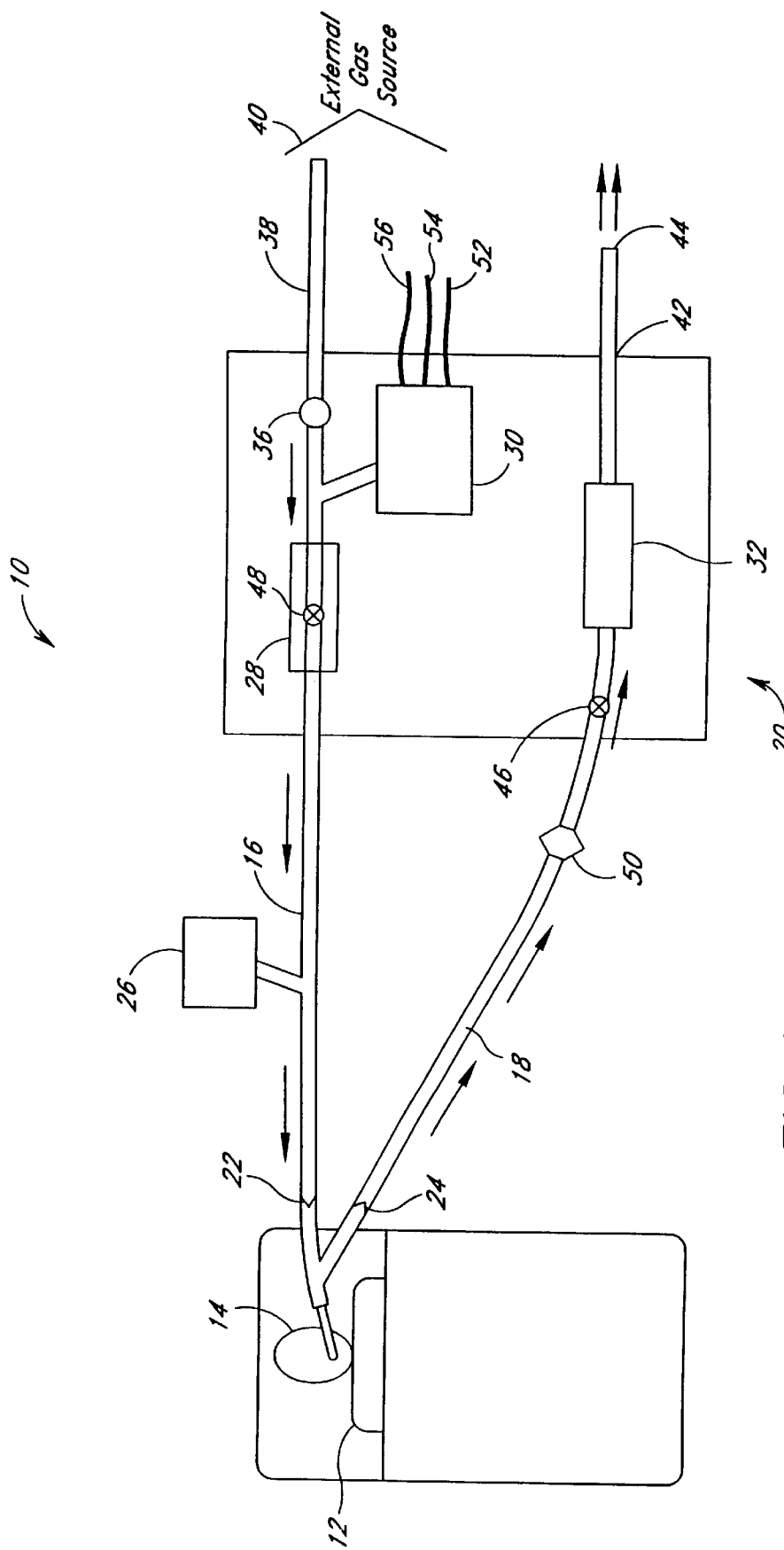
FIG. 1 is a schematic representation of a conventional prior art mechanical ventilation system.

While the present invention may be embodied in many different forms, disclosed herein are specific illustrative embodiments thereof that exemplify the principles of the invention. It should be emphasized that the present invention is not limited to the specific embodiments illustrated.

As those skilled in the pertinent arts will appreciate, the current invention teaches the use of vapor retention assemblies to reduce the loss of a respiratory promoter from the lungs over a period of time. In selected embodiments the vapor retention assembly may comprise a conventional heat and moisture exchanger. The invention also teaches novel vapor retainers comprising fluorophilic exchange elements in addition to, or in place of, conventional hygroscopic or hydrophilic exchange elements. Unlike prior art heat and moisture exchangers optimally designed to retain water vapor, the disclosed retention assemblies are particularly efficient at reducing the loss of a fluorinated compound from the lung due to evaporation. Accordingly, the methods and apparatus of the present invention may be used to sharply improve the efficiency of pulmonary therapies while driving down associated costs. Moreover, the invention reduces the discomfort of the patient by decreasing the number of interruptions in ventilatory therapy while, at the same time, lowering the burden on the care giver.

Those skilled in the art will further appreciate that the disclosed methods and apparatus may advantageously be used any time a respiratory promoter is introduced into the lungs. As previously discussed, the respiratory promoter may be any liquid, gaseous liquid or vapor that improves the pulmonary exchange of physiological gases. Preferably, the respiratory promoter is administered in the form of a free flowing liquid, vapor, suspension, mist or aerosol. In particularly preferred embodiments the respiratory promoter is a breathing liquid and in especially preferred embodiments a fluorochemical. It should also be emphasized that the present invention may be used in conjunction with any type of mechanical ventilation (including patient initiated assisted ventilation) or when the subject is breathing spontaneously. In either case, the disclosed methods and apparatus can substantially reduce the loss of the introduced respiratory promoter over the course of the treatment.

In particularly preferred embodiments the respiratory promoter will be a liquid introduced for the purpose of performing partial liquid ventilation, facilitate the pulmonary administration of a bioactive agent or perform bronchoalveolar lavage. Partial liquid ventilation or PLV as described in Fuhrman, U.S. Pat. No. 5,437,272, Faithfull, U.S. Pat. No. 5,490,498 and co-pending U.S. patent application Ser. No. 08/180,700 all incorporated herein by reference, has a number of benefits over conventional gas ventilation. The lungs are bathed in a biocompatible breathing fluid thereby minimizing lung trauma and permitting lung maturation or repair. Moreover, partial liquid ventilation is extremely amenable with conventional therapies since air or gas is still inhaled and exhaled. The amount of air entering the lungs on inhalation is sufficient to oxygenate, at least in part, the breathing liquid contained therein. Further, in preferred embodiments, the breathing liquid may be oxygenated prior to use to provide oxygen to the alveolar surfaces upon initial contact. As previously discussed, partial liquid ventilation can be used in conjunction with either spontaneous breathing or mechanical ventilation systems such as the one shown in FIG. 1. In addition, pharmacologic substances can be added to the respiratory promoter to further enhance resolution of pulmonary and systemic disorders.

In the following discussion common medical terms for the orientation of a ventilatory system will be used. Accordingly, the "distal" end of a system component, conduit or other element will be the farthest away from the attached patient while the "proximal" end or section is the closest to the patient. Moreover, as used herein, the term "patient" applies to any respiring mammalian subject including livestock, pets and other animals as well as humans.

Referring now to the drawing Figures, FIG. 1 provides a schematic representation of a conventional mechanical ventilation system 10 illustrating the principal features thereof. With respect to the instant invention, FIG. 1 represents a ventilation system that may be used in conjunction with a respiratory promoter and, in particular, with partial liquid ventilation. In the Figure, mechanical ventilation system 10 is connected to a patient 12 through a patient-connector 14. Typically, patient-connector 14 will comprise an endotracheal tube or a mask that allows gas, vapors and liquids to be administered to the lungs of the patient. In the illustrated apparatus, the distal end of patient-connector 14 branches to form a Y-connector providing two separate distal connecting ports. The distal connecting ports are sealingly attached to the proximal ends of inspiratory ventilating conduit 16 and expiratory ventilating conduit 18 respectively. For the purposes of this application the terms "conduit" or "ventilating conduit" will be held to mean any hose, tube, bore, lumen, shaft or other void containing structure capable of defining a fluid flow path. Those skilled in the art will appreciate that exemplary inspiratory ventilating conduit 16 and expiratory ventilating conduit 18 are typically formed of biocompatible flexible tubing having annular reinforcements to prevent kinking or blockage. Moreover, such ventilating conduits may be formed of materials compatible with specific respiratory promoters. Inspiratory ventilating conduit 16 defines a gas flow path comprising a lumen or bore which is capable of transporting gas to patient-connector 14 where it is introduced into the pulmonary air passages. Similarly, expiratory ventilating conduit 18 defines a gas flow path that may be used to transport exhaled or expiratory gas away from patient 12. Taken together ventilating conduits 16 and 18 comprise a ventilating circuit which, when connected with patient-connector 14 define a respiratory gas flow path. Arrows 58 illustrate the flow of gas through the system.

As with all commercially available mechanical ventilators, mechanical ventilation system 10 relies on pressurized gas source 40 for pneumatic power. In conventional mechanical ventilators pressurized gas source 40 is provided by an external bulk gas delivery system (i.e. pressurized tanks) or an internal compressor (not shown) which pressurizes air from the surrounding environment. In either case, pressurized air enters mechanical ventilation system 10 through inlet conduit 38 and pressure regulator 36. Although air from the pressurized gas source is typically on the order of 50 lb/in$^2$, pressure regulator 36 reduces this to a working pressure of approximately 1.5 lb/in$^2$ prior to employing it in mechanical ventilation system 10. Following the reduction of pressure the gas enters the distal or upstream end of inspiratory ventilating conduit 16.

Ventilating conduits 16 and 18 are operably associated with conventional mechanical ventilator apparatus 20. By "operably associated" it is meant that gas flow and ventilation operations using conduits 16 and 18 may be controlled, monitored and effected by ventilator apparatus 20. To this end ventilator apparatus 20 comprises inspiratory sensor assembly 28 and expiratory sensor assembly 32 which monitor and control gas flow and/or gas composition through inspiratory ventilating conduit line 16 and expiratory ventilating conduit line 18 respectively. Among other data, sensor assemblies 28 and 32 provide real time information regarding gas composition, temperature, pressure and flow rate. Accordingly, gas entering inspiratory ventilating conduit 18 is monitored by inspiratory sensor assembly 28. Based on the readings, gas injector 30 may be signaled or manually set to introduce oxygen or other gases to the gas flow path defined by inspiratory ventilating conduit 18. Transfer lines 52, 54, 56 provide gas injector 30 with access to external sources of oxygen, nitrogen or other selected gases. Those skilled in the art will appreciate that gas injector 30 may operate using preprogrammed instructions or may be controlled by ventilator apparatus 20 based on information from sensor assemblies 28 and 32 or using preset values.

Gas flow and pressure through conduits 16 and 18 is physically controlled through inspiratory flow valve 48 and optional expiratory flow valve 46 which are opened and closed based on preprogrammed instructions and information received from sensor assemblies 28 and 32. Those skilled in the art will appreciate that flow valves 46 and 48 may comprise any of a number of different types of valves including solenoid valves, digital solenoid valves and full-range proportional valves. As will be described below, flow valves 46 and 48 will be manipulated to provide the desired wave form and pressure for ventilation. Passing downstream through inspiratory flow valve 48 the inspiratory gas may be modified by humidifier 26 which introduces vapor to the gas flow path. As with gas injector 30, humidifier 26 may be controlled by preprogrammed instructions manual settings or by ventilator apparatus 20. The inspiratory gas, now containing adequate oxygen and water vapor is then transported along the gas flow path through one arm of patient-connector 14 and into patient 12. Optional inspiratory check valve 22 may be provided to ensure the directional travel of the inspiratory gas.

Following introduction of the inspiratory gas into the pulmonary air passages (not shown) of patient 12 under positive pressure, ventilation is effected upon distribution of the gas in the lungs to promote gas exchange and oxygenation. Those skilled in the art will appreciate that the fresh oxygen from the inhaled inspiratory gas crosses the alveoli and enters the blood while waste gases (carbon dioxide, etc.) are excreted from the body. As previously alluded to, a respiratory promoter (preferably comprising a fluorochemical) may be present in the pulmonary passages of patient 12 to facilitate the uptake of oxygen and excretion of waste gases. While oxygen passes into the bloodstream, waste gases simultaneously collect in the lungs. When using conventional mechanical ventilators, such as the one shown in FIG. 1, the introduction of inspiratory gas will typically be pulsed or cycled. As previously discussed this introductory period is known as the inspiratory phase of the breathing cycle. During the lull between the introduction of gases, the lungs return to ambient pressure and deflate due to tension on pulmonary passages from surrounding tissue. This contraction of the lungs and corresponding reduction in lung volume forces accumulated gases and vapors, collectively known as expiratory gas, from the lungs. In the case of traditional gas ventilation the exhaled expiratory gas will comprise unused oxygen and waste gases including carbon dioxide. When a respiratory promoter has been introduced into the lung of the patient, such as when performing PLV, the exhaled gas will typically comprise vaporized respiratory promoter in addition to unrespired oxygen and waste gases.

The spontaneous contraction of the lungs forces the exhaled gas into patient-connector 14, preferably sealingly connected to patient 12. Unidirectional inspiratory check valve 22 prevents the expiratory gas from substantially entering inspiratory ventilating conduit 16. Instead the expiratory gas is directed through unidirectional expiratory check valve 24 into expiratory ventilating conduit 18. From here the expiratory gas travels along the gas flow path defined by expiratory ventilating conduit 18, through optional flow control valve 46, and into ventilator apparatus 20. Optionally, the expiratory gas may be passed through conventional filter 50, positioned anywhere along expiratory ventilating conduit 16, wherein pathogenic organisms and other undesirable material may be removed from the expiratory gas. After entering ventilator apparatus 20 the gas flow path passes through sensor assembly 32 wherein data may be gathered regarding the composition and flow of the expiratory gas as well as the breathing cycle. Those skilled in the art will appreciate that the schematic representation of the sensors in FIG. 1 is exemplary only and that any sensors employed in ventilator apparatus 20, including those compatible with the present invention may collect the desired information using any effective means. Passing through ventilator apparatus 20 in the gas flow path defined by expiratory ventilating conduit 18 the expiratory gas proceeds through outlet conduit 42 and is vented into the surrounding environment through exhaust aperture 44. Unfortunately, any respiratory promoter exhaled by the patient is also vented necessitating replacement to effectively continue the therapeutic regimen.

Curtailing this loss of respiratory promoter and corresponding degradation in therapeutic efficacy without incurring significant costs or unduly complicating ventilation procedures is a major advantage of the present invention. More specifically, as illustrated by a preferred embodiment of the invention shown in FIG. 2, the disclosed methods and apparatus may be used in conjunction with conventional ventilation systems to markedly improve ventilation procedures incorporating the pulmonary administration of a respiratory promoter. That is, while not required to practice the invention, respiratory gas exchange may be maintained by continuous positive pressure ventilation using a conventional ventilator. By "continuous positive pressure ventilation" is meant positive pressure mechanical ventilation, often with positive end-expiratory pressure, that may be accomplished by any standard positive pressure ventilator. Either volume regulated, time-cycled respirators or pressure-limited time-cycled respirators are compatible with the instantly disclosed processes and apparatus. Examples of commercially available ventilators that are compatible with the present invention include, but are not limited to, Servo 900C (Seimens Elema, Shaumburg, Ill.), Infant Star (Star Products, San Diego, Calif.), Bear 1,2,3 (Bear Medical, Browns, Calif.), Puritan-Bennett 7200, (Puritan-Bennett Corp., Carlsbad, Calif.) Baby Bird 2 (Bird Corp., Calif.), and the Healthdyne Infant Ventilator. Of course, the disclosed methods and apparatus are entirely compatible with procedures involving the pulmonary administration of a respiratory promoter in the absence of a ventilator.

Performing PLV in accordance with the present invention may comprise the administration of very low doses (on the order of 0.005 mL/kg or less) of respiratory promoter preferably incorporating the desired fluorochemical or combination of fluorochemicals. Essentially, a therapeutically effective amount comprises enough to form a thin coating on a portion of the lung. Preferably the volume should be substantially equivalent to about 0.01% to about 100% of the normal pulmonary functional residual capacity (FRC) of the host. By "pulmonary functional residual capacity" is meant the volume of space in the pulmonary air passages at the end of expiration. That is, the amount of breathing liquid used for partial liquid ventilation may approximate the volume of air remaining in a healthy lung of similar size following exhalation, or alternatively, that volume plus the volume of the endotracheal tube. It will further be appreciated by those skilled in the art that preferred volumes may be within certain ranges. Thus, selected embodiments of the invention include administration of fluorochemical of 0.01–1%, 0.01–10%, 1%–10%, 1–20%, 5–50%, 10–70%, 50–75%, 50–100% and 75–100% of the host's pulmonary FRC, calculated using standard methods known in the art. Of course the recited ranges are approximations only and the amount of introduced breathing liquid may fluctuate beyond the recited ranges during therapy. In practice the actual volumes will depend on the treatment protocol, the weight and size of a patient, as well as the lung capacity. Delivery of fluorochemical to a single lobe (unilateral) or local portion (lobar, segmental) is also contemplated.

In a particularly preferred embodiment of the present invention the desired amount of fluorochemical is administered to the lung and the ventilation system comprising a vapor retention assembly is attached. Respiratory therapy is begun, preferably with positive pressure ventilation, with the atmosphere in the lung quickly becoming saturated with vaporized breathing liquid. The system incorporated vapor retainer acts to maintain this pulmonary saturation. Preferably, the process is monitored by sensors in the ventilation system and a vapor analyzer is used to control the amount of breathing liquid added to the pulmonary passages to maintain the desired volume. Following completion of the therapy the system is removed and the respiratory promoter is typically allowed to evaporate.

In another preferred embodiment, the aforementioned process is carried out without the preliminary administration of fluorochemical to the lung. Rather the respiratory promoter is added to the ventilation system preferably in a nebulized or vaporized form, following connection with the patient. Preferably the respiratory promoter will be added upstream of the vapor retention assembly, i.e. into patient-connector 114. Again the pulmonary environment reaches substantial equilibrium that may be easily maintained by small additions of material from a nebulizer or gas injector. This method is particularly preferred for PLV involving the pulmonary introduction of respiratory promoter at volumes less than functional residual capacity of the patient.

As discussed above, PLV may be undertaken using any respiratory promoter which provides the desired pulmonary therapeutic response. Preferably, the respiratory promoter is a breathable liquid in the form of a fluid, aerosol, vapor or mist. For example, in some indications hyperoxygenated saline may be used as a breathing liquid in accordance with the present invention. More preferably however, PLV will be performed using a breathing liquid comprising a fluorochemical. Particularly preferred embodiments employ fluorochemicals that are liquid at body temperature.

By "fluorochemical" is meant any fluorinated carbon compound with appropriate physical properties of biocompatibility. These properties are generally met by fluorochemicals having low viscosity, low surface tension, low vapor pressure, and high solubility for oxygen and carbon dioxide making them able to readily promote gas exchange while in the lungs. For example, it is preferred that the fluorochemical have at least 3 or 4 carbon atoms and/or that its vapor pressure at 37° C. is less than 760 Torr. The fluorochemical may be made up of atoms of carbon and fluorine, or may be a fluorochemical having atoms other than just carbon and fluorine, e.g., bromine or other nonfluorine substituents. Those skilled in the art will appreciate that the range of compatible fluorochemicals is substantially broadened by the present invention.

More particularly, one of the major advantages of the present invention is that the incorporation of a vapor retention assembly allows the extended therapeutic use of fluorochemicals that were previously too volatile to use effectively. Previously, some volatile fluorochemicals were used for short term drug therapy where pulmonary retention time was not critical. With the present invention, relatively high vapor pressure fluorochemicals may be used effectively as their rate of loss by evaporation is substantially reduced. That is, the incorporation of vapor retention assemblies in ventilation systems promotes the conservation of breathing liquids including volatile fluorochemicals. Accordingly, steady pulmonary levels of these fluorochemicals are rapidly reached and easily maintained using the ventilation systems described herein.

Representative fluorochemicals useful in the present invention include bis(F-alkyl) ethanes such as $C_4F_9CH$=$CH_4CF_9$ (sometimes designated "F-44E"), i-$C_3F_9CH$=$CHC_6F_{13}$ ("F-i36E"), and $C_6F_{13}CH$=$CHC_6F_{13}$ ("F-66E"); cyclic fluorochemicals, such as C10F18 ("F-decalin", "perfluorodecalin" or "FDC"), F-adamantine ("FA"), F-methyladamantane ("FMA"), F-1,3-dimethyladamantane ("FDMA"), F-di-or F-trimethylbicyclo [3,3,1]nonane ("nonane"); perfluorinated amines, such as F-tripropylamine ("FTPA") and F-tri-butylamine ("FTBA"), F-4-methyloctahydroquinolizine ("FMOQ"), F-n-methyl-decahydroisoquinoline ("FMIQ"), F-n-methyldecahydroquinoline ("FHQ"), F-n-cyclohexylpurrolidine ("FCHP") and F-2-butyltetrahydrofuran ("FC-75" or "RM101")

Brominated fluorochemicals compatible with the teachings herein include 1-bromo-heptadecafluoro-octane ($C_8F_{17}Br$, sometimes designated perfluorooctylbromide or "PFOB"), 1-bromopenta-decafluoroheptane ($C_7F_{15}Br$), and 1-bromotridecafluorohexane ($C_6F_{13}Br$, sometimes known as perfluorohexylbromide or "PFHB"). Other brominated fluorochemicals are disclosed in U.S. Pat. No. 3,975,512 to Long. Also contemplated are fluorochemicals such as perfluorooctyl chloride, perfluorooctyl hydride, and similar compounds having different numbers of carbon atoms.

Additional fluorochemicals contemplated in accordance with this invention include perfluoroalkylated ethers or polyethers, such as $(CF_3)_2CFO(CF_2CF_2)_2OCF(CF_3)_2$, $(CF_3)_2$ $CFO$-$(CF_2CF_2)_3OCF(CF_3)$, $(CF_3)CFO(CF_2CF_2)F$, $(CF_3)_2$ $CFO(CF_2CF_2)_2F$, $(C_6F_{13})_2O$. Further, fluorochemical-hydrocarbon compounds, such as, for example, compounds having the general formula $C_nF_{2n+1}$-$C_{n'}F_{2n'+1}$, $C_nF_{2n+1}$ $OC_{n'}F_{2n'+1}$, or $C_nF_{2n+1}CF$=$CHC_{n'}F_{2n'+1}$, where n and n' are the same or different and are from about 1 to about 10 (so long as the compound is a liquid at room temperature). Such compounds, for example, include $C_8F_{17}C_2H_5$ and $C_6F_{13}CH$=$CHC_6H_{13}$.

It will be appreciated that esters, thioethers, and other variously modified mixed fluorochemical-hydrocarbon compounds are also encompassed within the broad definition of "fluorochemical" liquids suitable for use in the present invention. Mixtures of fluorochemicals are also contemplated and are considered to fall within the meaning of "fluorochemicals" as used herein. Additional fluorochemicals contemplated are those having properties that would lend themselves to pulmonary gas exchange including FC-75, FC-77, RM-101, Hostinert 130, APF-145, APF-140, APF-125, perfluorodecalin, perfluorobutyl-tetrahydrofuran, perfluoropropyl-tetrahydropyran, dimethyl-adamantine, trimethyl-bicyclo-nonane, and mixtures thereof.

In particular, preferred fluorochemicals are characterized by having: (a) an average molecular weight range from about 350 to about 570; (b) viscosity less than about 5 centipoise at 25° C.; (c) boiling point greater than about 55° C.; (d) vapor pressure in the range from about 5 to about 75 Torr, and more preferably from about 5 to about 50 Torr, at 25° C.; (e) density in the range of about 1.6 to about 2 gm/cm$^3$; and (f) surface tensions (with air) of about 12 to about 20 dyne/cm.

Figure 2:
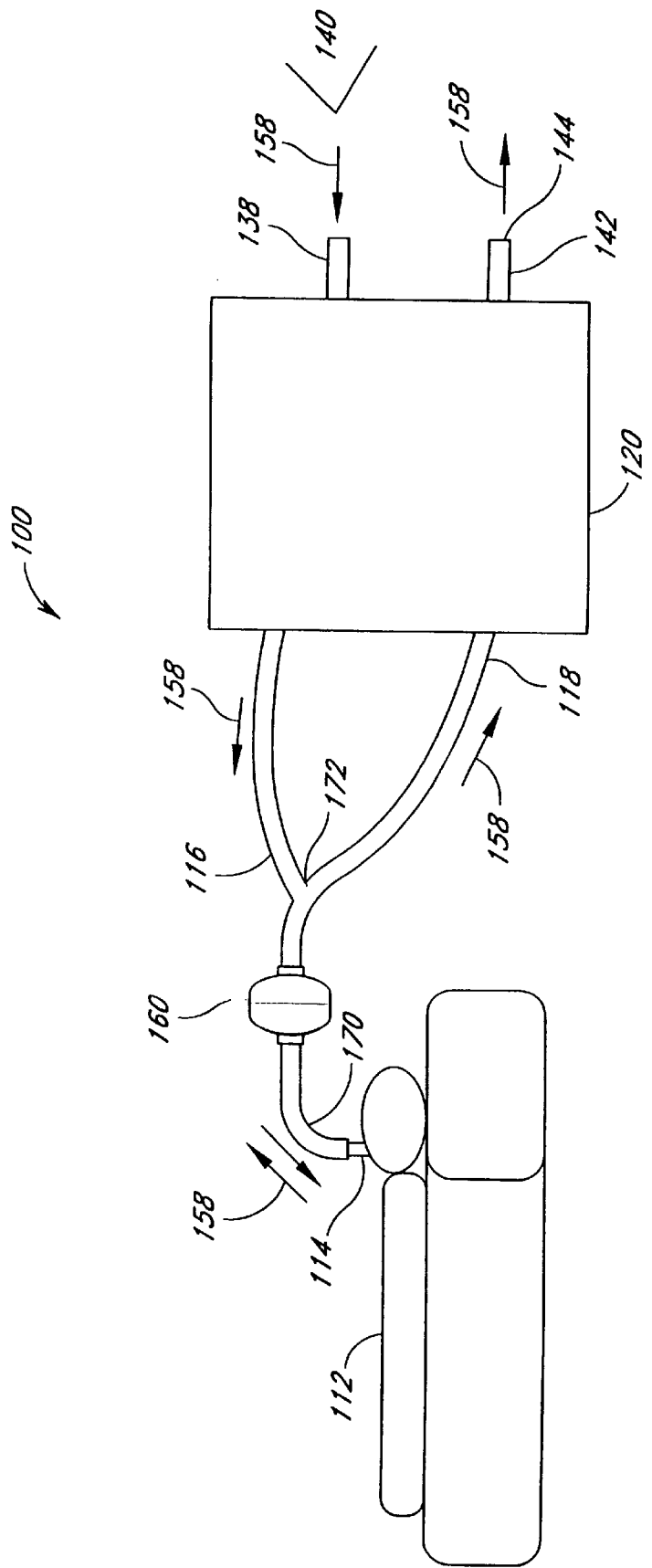
FIG. 2 is a schematic representation of an exemplary ventilating system comprising a vapor retention assembly in accordance with the present invention.

Turning now in detail to FIG. 2, a preferred embodiment of the present invention comprising the mechanical ventilation system of FIG. 1 is depicted. Yet, unlike the conventional ventilation system shown in FIG. 1, the ventilation system of FIG. 2 substantially reduces the loss of respiratory promoter in a connected patient. In the interest of brevity and to more accurately illustrate the novel aspects of present invention, some of the detail in FIG. 1 has been omitted. Those skilled in the art will appreciate that the omitted material, including gas injectors, pumps, check valves, etc., is compatible with the invention and may optionally be included in various embodiments thereof.

In particular, FIG. 2 schematically shows ventilation system 100 connected to patient 112 via patient-connector 114. Preferably, patient 112 has previously had a predetermined volume of at least one respiratory promoter, optionally comprising a bioactive agent, introduced into their lungs. Typically, patient-connector 114 comprises an endotracheal tube or mask that sealingly provides fluid-conducting communication between ventilation system 100 and the pulmonary air passages (not shown) of patient 112. As discussed above, breathing or inspiratory gas is forced (optionally with patient assistance) into the lungs of patient 112 using pulsed or cyclical positive pressure. Following respiration expiratory or exhaled gas, preferably comprising at least a portion of the introduced respiratory promoter in a vaporous state, is forced from the lung under pressure during spontaneous exhalation. The exhaled gas and entrained respiratory promoter pass through patient-connector 114 and patient-connector conduit 170 where they enter vapor retention assembly 160 which is in fluid conducting communication with the ventilating circuit formed by ventilating conduits 116 and 118.

As will be discussed in detail below, vapor retention assembly 160 reversibly associates with, and retains, at least part of the exhaled respiratory promoter. The modified expiratory gas, having a lower concentration of vaporized respiratory promoter than was present when the gas was initially exhaled, then passes from vapor retention assembly 160, through Y-connector 172 and enters expiratory ventilation conduit 118 as shown by arrows 158. A series of check valves (not shown) controls the flow of gas through ventilation system 100. Passing through expiratory ventilation conduit 118 and mechanical ventilator 120 substantially as described with respect to FIG. 1, the modified exhaled gas is forced through outlet conduit 142 and is vented into the surrounding environment through exhaust aperture 144. Alternatively, the modified expiratory gas may be captured or further treated using filters or traps (not shown) designed to remove any remaining respiratory promoter following venting.

In order to effect respiration and keep patient 112 alive, a breathing gas must be introduced to the pulmonary air passages following the expiratory phase of the respiration cycle. To that end a breathing or inspiratory gas is interjected into the lungs of patient 112 using pulsed or cyclical positive pressure provided by mechanical ventilator 120. Typically, the breathing gas introduced into ventilation system 100 does not comprise a respiratory promoter. As with the ventilation system shown in FIG. 1, pressurized gas source 140 forces a breathing gas into mechanical ventilation system 100 through inlet conduit 138. Optional pressure regulators, pumps, valves, etc. (not shown) drive the pressurized breathing gas unidirectionally through mechanical ventilator 120 and inspiratory ventilating conduit 116 as shown by gas flow arrows 158. The oxygen-containing breathing gas then passes through Y-connector 172, into patient-connector conduit 170 and enters vapor retention assembly 160. Upon passing through vapor retention assembly 160 the oxygen-containing breathing gas entrains at least a portion of the respiratory promoter associated with retention assembly 160 during the expiratory phase of the preceding respiratory cycle. The oxygen-containing breathing gas, still driven by ventilator 120 and now enriched with vaporized respiratory promoter, passes from vapor retention assembly 160 through patient-connector conduit 170 and patient-connector 114 and into the pulmonary air passages of patient 112.

Those skilled in the art will appreciate that the vapor retainers may be positioned anywhere in fluid conducting communication with the gas flow path. That is they do not have to be place proximally of the Y-connector. Specifically, selected embodiments (not shown) of the present invention use a plurality of vapor retainers operating in concert to effect pulmonary retention of the introduced respiratory promoter. In such embodiments a first vapor retainer may be in fluid conducting communication with the inspiratory ventilation conduit distal from the patient connector while a second vapor retainer may be in fluid conducting communication with the expiratory ventilation conduit. Following exhalation and association of the respiratory promoter with the second vapor retainer, the retainers would be rotated or switched so that the first vapor retainer would be in fluid conducting communication with the expiratory conduit while the second vapor retainer would be in fluid conducting communication with the inspiratory conduit. Upon passing a breathing gas through the second vapor retainer the previously associated respiratory promoter would be entrained in the gas and delivered to the lungs of a patient. Use of such a configuration would allow a reduction in the "dead space" typically found in vapor retainers. Those skilled in the art will appreciate that the dead space or volume is that volume of expiratory gas that failed to clear the vapor retainer and is inhaled on the subsequent breath.

In preferred embodiments the vapor retention assemblies would be arranged axially about a rotational center. For example the vapor retainers could be arranged about the periphery of a drum attached to a motor. The rotation of the drum and switching of the vapor retention assemblies preferably would be coordinated or synchronized with breathing cycle of the patient. Seals and check valves would be used to ensure the continued integrity of the ventilating circuit during the switching process. Further, a purge element could optionally be added to introduce oxygen and/or respiratory promoter into the selected vapor retainer prior to integration into the inspiratory conduit thereby reducing any dead space even more.

Figure 3:
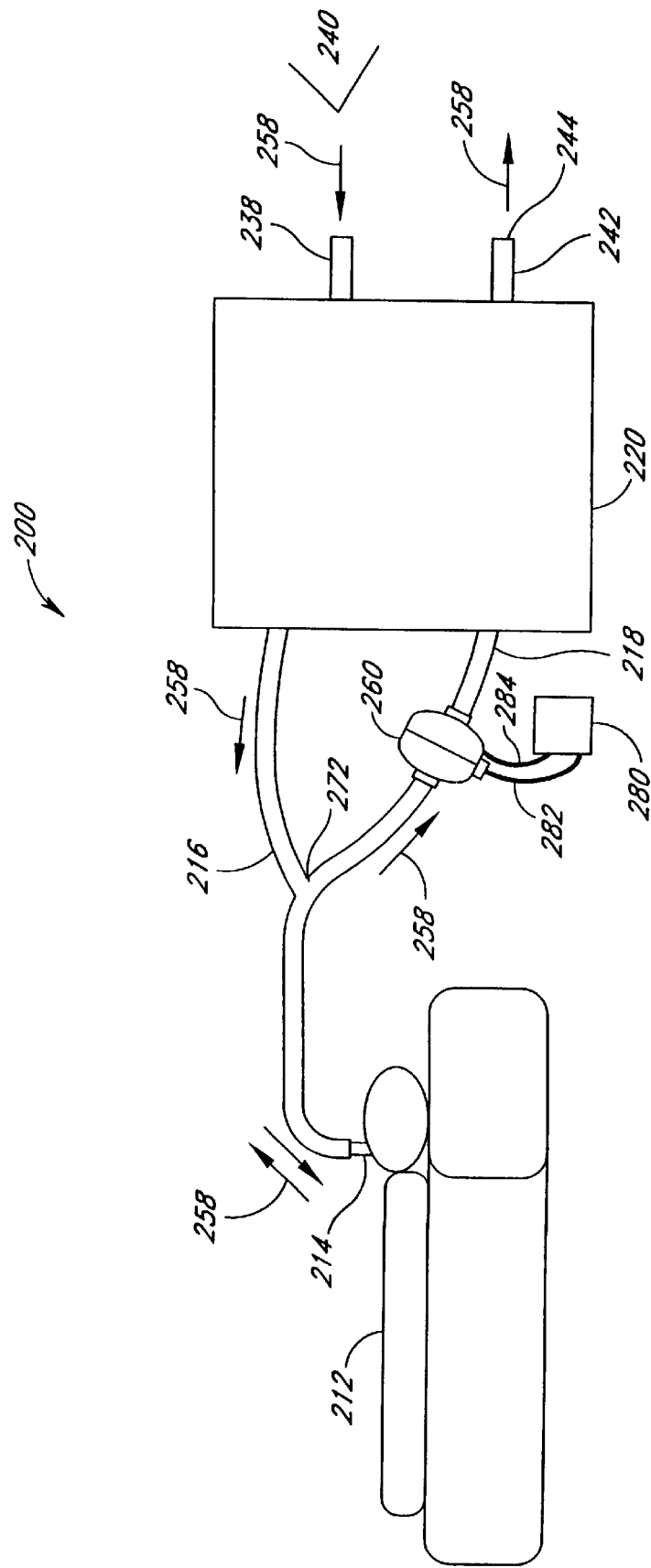
FIG. 3 is a schematic representation of an exemplary ventilating system comprising a vapor retention assembly in a suitable configuration for the ex vivo recovery of a respiratory promoter.

Another embodiment of the present invention, providing for the recovery of a respiratory promoter rather than immediate patient reintroduction is shown in FIG. 3. As those skilled in the art will appreciate the embodiment of the invention illustrated in FIG. 3 is similar to that shown in FIG. 2. More specifically FIG. 3 shows patient 212 connected to ventilation system 200 via patient-connector 214. The pulmonary air passages of patient 212, preferably containing at least one respiratory promoter, are in fluid conducting communication with ventilation system 200. As with the embodiment of FIG. 2, pressurized breathing gas enters ventilation system 200 through inlet conduit 238 and passes through ventilator 220 and inspiratory ventilation conduit 216. Those skilled in the art will appreciate that the introduced breathing gas is typically air but could be any oxygen containing composition. Optional check valves, pressure controllers, gas injectors, humidifiers and vaporizers capable of delivering respiratory promoter (not shown) accurately control the flow and composition of the pressurized breathing gas. Significantly, the breathing gas does not pass through a vapor retention assembly. Following inspiratory ventilation conduit 216 the breathing gas (optionally supplemented with respiratory promoter and water vapor) passes through Y-connector 272 and patient-connector 214 before being inhaled by patient 212 and entering the pulmonary air passages wherein physiological gas exchange is facilitated by the respiratory promoter.

After the inspiratory phase of the respiratory cycle is completed and waste gases are excreted by patient 212, the expiratory gas is exhaled through spontaneous contraction of the lung tissue. The exhaled gas, comprising a portion of the introduced respiratory promoter in a vaporized state, then leaves the pulmonary air passages of patient 212 and passes through patient-connector 214 and Y-connector 272 where it enters expiratory ventilating conduit 218. Passing through expiratory ventilating conduit 218 the exhaled gas enters vapor retention assembly 260 comprising an exchange element (not shown) in fluid conducting communication with expiratory ventilating conduit 218. As the exhaled gas contacts the exchange element, at least a portion of the vaporized respiratory promoter is reversibly associated with the element. The exhaled gas, now comprising a lower concentration of respiratory promoter then exits vapor retention assembly 260, passes through the distal portion of expiratory ventilation conduit 218, ventilator 220 and outlet conduit 242 before being vented through exhaust aperture 244. As alluded to earlier, the exhaled gas may be vented into the surrounding environment or, optionally, directed into a filter or trap wherein the remaining respiratory promoter is recovered.

In any case recovery of the respiratory promoter is also undertaken from vapor retention assembly 260. With respect to the embodiment shown in FIG. 3, recovery apparatus 280 is in fluid conducting communication with vapor retention assembly 260 through injection line 284 and recovery line 282. As described above, at least a portion of the vaporized respiratory promoter in the exhaled gas is reversibly associated with the exchange element as the gas passes through vapor retention assembly 260. The breathing gas, typically air, is circulated through vapor retention assembly 260 and, after evaporating at least a portion of the associated respiratory promoter, is returned to recovery apparatus 280 where the respiratory promoter is separated. More particularly air, or another transport gas that need not contain oxygen, is supplied by recovery apparatus 280 and forced under pressure through injection line 284 into vapor retention assembly 260. Those skilled in the art will appreciate that any source may be used to provide and inject the transport gas and that the embodiment shown in FIG. 3 is in no way limiting. It will further be appreciated that the transport gas is preferably injected so as not to interfere with the patient's breathing cycle. This may be accomplished, for instance, by injecting the transport gas during the inspiratory phase of the patient's breathing cycle. One-way check valves (not shown) in the proximal section of expiratory ventilating conduit 218 may be used to prevent the pressurized transport gas from entering the pulmonary air passages of patient 212.

Preferably the transport gas will be introduced and will exit vapor retention assembly 260 through ports other than those used to introduce and remove the exhaled gas. Following introduction, the transport gas will contact the exchange element of vapor retention assembly 260 and vaporize or otherwise entrain at least a portion of the associated respiratory promoter. The transport gas, now comprising respiratory promoter, is then forced through a port in vapor retention assembly 260 and into recovery line 282 where it is transported to recovery apparatus 280. After the transport gas is introduced into recovery apparatus 280, the respiratory promoter is separated and isolated. Although the respiratory promoter may be recovered using any one of a number of different techniques, active condensation is preferably used to separate the desired promoter from the transport gas. Suitable condensation methods incorporating cooling elements for removing vaporized respiratory promoters (particularly fluorochemicals) from exhaled gases are described in co-pending U.S. patent application Ser. No. 08/180,700 already incorporated herein. Typically, the respiratory promoter will be liquefied and stored in a reservoir (not shown) where it may be processed to remove water and other unwanted pulmonary debris. In any case, the recovered respiratory promoter may be reintroduced into the lungs of patient 212 using techniques known to those skilled in the art or treated and introduced into other patients.

Further, it will be appreciated that respiratory promoter associated with the exchange element of vapor retention assembly 260 may be recovered without employing recovery apparatus 280. For example, the volume of associated respiratory promoter may build to the point where it spontaneously forms droplets which coalesce and flow to the lowest point of vapor retention assembly 260 due to gravitational effects. In selected embodiments vapor retention assembly 260 could be fitted with a drain (not shown) that allows the liquefied respiratory promoter to flow directly into a collection reservoir. Alternatively, the liquefied respiratory promoter could be aspirated from vapor retention assembly 260 through a collection port (not shown) and stored in a collection reservoir. Either way, the collected respiratory promoter may be treated and reintroduced or stored as described above.

It must be emphasized that the embodiments of the invention employing a ventilation system comprising a mechanical ventilator are exemplary only and do not, in any way, limit the scope of the subject matter disclosed herein. More specifically, those skilled in the art will appreciate that the disclosed methods and apparatus are entirely compatible with ventilation techniques that do not use a mechanical ventilator. For example, a spontaneously breathing patient may be fitted with a mask or other patient-connector comprising a vapor retention assembly in accordance with the present invention. Yet, in this case the vapor retention assembly would not be a component of a mechanical ventilation system but rather would introduce and discharge inspiratory and expiratory gases directly into the surrounding environment.

In particular, at least one respiratory promoter would be introduced into the lungs of a naturally respiring patient. A mask or other patient-connector comprising a vapor retention assembly having at least one exchange element would be fitted so as to establish fluid conducting communication with the pulmonary air passages. Upon exhalation expiratory gas comprising vaporized respiratory promoter would be forced from the lungs and pass through the patient-connector to the vapor retention assembly. As the warm expiratory gas passes through the vapor retention assembly at least a portion of the vaporized respiratory promoter is reversibly associated with the exchange element. The treated exhaled gas then passes from the vapor retention assembly into the surrounding atmosphere to conclude the expiratory phase of the breathing cycle. At the start of the inspiratory phase the lungs expand to draw in breathing gas from the environment. Note that, in this embodiment, no ventilator is required to force air into the lungs of the patient. As the patient inhales, relatively dry cool air devoid of respiratory promoter is drawn into the vapor retention assembly and contacts the exchange element causing the associated respiratory promoter to evaporate. The inhaled air, now comprising vaporized respiratory promoter is then drawn through the patient-connector and into the pulmonary air passages where respiration occurs. The cycle is then repeated beginning with the start of the next expiratory phase. Of course it will be appreciated that additional respiratory promoter may be added periodically to maintain the desired pulmonary levels. Such methods are particularly useful for treatments conducted outside a hospital critical care setting such as in emergency situations or in the home.

The present invention is not limited to methods of performing liquid ventilation. In particular, the disclosed methods and apparatus provide for the independent delivery of pharmaceutical agents or their use in conjunction with other vapors or liquids such as respiratory promoters. Moreover, the devices and methods of the present invention may be used for the therapeutic administration of pharmaceutical agents in conjunction with spontaneous breathing or mechanical ventilation. In particular, combining pharmaceutical dosing regimens with liquid ventilation therapy has a number of advantages over other forms of drug delivery. The fluorochemical-enhanced delivery can be used for medicaments that would otherwise be ineffective or destroyed by systemic delivery. For example, those skilled in the art will appreciate that proteins usually cannot be administered orally because they are destroyed in the alimentary tract. Some proteins may invoke severe allergic reactions and shock in the host if administered through systemic routes such as intramuscularly or intravenously.

In particularly preferred embodiments antibiotics, antivirals and chemotherapeutic agents may be provided in combination with a fluorochemical liquid during partial liquid ventilation. As an example of such treatments it is well known that the pathogenic cytomegalovirus can induce life-threatening cases of pneumonia in immunocompromised patients. These individuals often require ventilation therapy to stay alive. The administration of a respiratory promoter, particularly a fluorochemical, in combination with the guanosine nucleoside analog, 9-(1,3-dihydroxy-2-propoxymethyl)guanine, otherwise known as Ganciclovir or DHPG, may provide an effective therapy that could simultaneously inhibit viral replication and facilitate oxygen transport in the compromised lung.

The precise amount of pharmaceutical agent administered in conjunction with the methods and devices of the present invention is dependent upon the agent of choice, the required dose, and the form of the drug actually introduced. Those skilled in the art will appreciate that such determinations may be made by using well-known techniques in combination with the teachings of the present invention.

Preferred pharmaceutical agents for use in the present invention comprise respiratory agents, antibiotics, antivirals, mydriatics, anti-inflammatories, antihistaminics, antineoplastics, anesthetics, cardiovascular agents, active principles, nucleic acids, genetic material, immunoactive agents, imaging agents, immunosuppressive agents, etc. and combinations thereof.

In addition to enhanced drug delivery, liquid mediums such as fluorochemicals can be used to remove endogenous or foreign material from the interior of the lungs in accordance with the present invention. Fluorochemicals can be substituted for conventional physiological saline solutions used in lavage and may be introduced as described herein. Such techniques are particularly compatible with the embodiment of the invention shown in FIG. 3. Because fluorochemicals are oxygenatable, they provide oxygen to the person during the treatment allowing for longer and less dangerous lavage procedure. The density of fluorochemical liquids is generally twice that of water and body tissue which permits the fluorochemical to sink below and displace the material to be removed. Then when the fluorochemical is removed by mechanical means well known in the practice of lavage, the displaced material will float and be removed simultaneously. These properties are particularly important when lavage is combined with liquid ventilation-enhanced drug delivery as a complete treatment of, for example, a patient with cystic fibrosis whose lungs accumulate excess mucinous secretions.

Yet, whichever therapeutic regimen is practiced using the present invention, reducing the loss of respiratory promoter from the lungs is contingent on the use of at least one vapor retention assembly. In accordance with the teachings herein, compatible vapor retention assemblies may be either commercially available heat and moisture exchangers or novel fluorophilic units comprising a fluorophilic exchange element. Those skilled in the art will appreciate that commercially available heat and moisture exchangers were designed and fabricated to optimize the pulmonary retention of water vapor. While not limiting the invention in any way, it is believed that conventional heat and moisture exchangers associate with respiratory promoters, and particularly fluorochemicals, primarily through localized thermodynamic fluctuations in the vapor retention assembly. More particularly, it is believed that the vapor rich exhaled gas is cooled in the vapor retention assembly causing adsorption or absorption of the respiratory promoter. Conversely, the novel vapor retention assemblies comprising a fluorophilic exchange element advantageously use molecular affinity to wet the element and increase the efficiency of the assemblies. Accordingly, while conventional heat and moisture exchangers comprising hygroscopic or electrostatic exchange elements are effective in reducing the loss of respiratory promoter, use of the disclosed fluorophilic assemblies can further reduce the rate of promoter loss. More particularly, conventional heat and moisture exchangers may reduce fluorochemical loss from approximately 20% to 40% while the novel fluorophilic exchange elements can reduce losses by more than 40%. This, in turn, increases the efficacy of the applied therapy.

Unless otherwise dictated by contextual restraints, the terms "heat and moisture exchanger" and "HME" are used herein to mean any exchange device typically used in ventilation or anesthesia systems to passively humidify a patient. Accordingly, as used herein, heat and moisture exchangers shall include, but not be limited to heat and moisture exchangers, heat and moisture exchanging filters, hygroscopic condenser humidifiers, and hygroscopic condenser humidifying filters. Specifically, it will be appreciated that both hygroscopic and electrostatic exchangers may be used in the disclosed methods. Heat and moisture exchangers compatible with the invention include the HEPA filtered Hygroscopic Condenser Humidifier (Baxter Healthcare Corp., Deerfield, Ill.), the AQUA+FH HCH with filter (Hudson RCI, Temecula, Calif.), the Intersurgical Heat and Moisture Exchanging Filter (Intersurgical, Inc. Liverpool, N.Y.), the Hygrobac Filter HME (Mallinckrodt Medical, Inc., St. Louis, Mo.), the Gibeck Humid-Vent Filter RT30+ and the Gibeck Humid-Vent 2s (Gibeck Respiration AB, Upplands Vasby, Sweden), the Meridian Medical Systems Heat and Moisture Exchange Filter (Meridian Medical Systems, Indianapolis, Ind.) and the Pall HME 15-22 (Pall Biomedical Products Corp., East Hills, N.Y.). The use of such exchangers provides the added advantage of retaining moisture into the lung thereby reducing the need to introduce water vapor in the ventilation system. In any case, it further will be appreciated by those skilled in the art that any heat and moisture exchanger comprising an exchange element capable of reversibly associating with the selected respiratory promoter is compatible with the invention and, accordingly, the foregoing list is exemplary only.

In addition to the aforementioned conventional heat and moisture exchangers, novel vapor retention assemblies comprising at least one fluorophilic exchange element are also compatible. As used herein, a fluorophilic exchange element is any element capable of absorbing, adsorbing or otherwise reversibly associating with a fluorochemical vapor upon contacting said vapor. Elements may be formed from any material exhibiting the proper characteristics including, for example, silicone. Other materials that may be used comprise urethane, fluoroelastomers, plastics such as polypropylene, polyethylene or polyesters, composite materials comprising thermoset or thermoplastic resins or any material containing at least one halogenated compound. In particularly preferred embodiments the fluorophilic exchange element comprises a fluorinated compound. Another preferred fluorophilic material is Delrin®.

It will be appreciated that the form of the fluorophilic exchange element is not critical and any construct that allows for the relatively efficient reversible association of the respiratory promoter is acceptable. As will be seen in the examples detailed below, preferred forms of the exchange elements comprise quilted disks or wafers, scrimmed materials, fibrous constructs, foams or other porous conformations and particulate constructions. Generally, those forms having a large surface area and a minimum resistance to air flow are preferred.

It will also be appreciated that the absolute configuration of the vapor retention assembly is not critical and may be selected to optimize the characteristics of the apparatus. In particular, the fluorophilic exchange element may be positioned in any configuration as long as it provides for effective contact between the gas passing through the vapor retention assembly and the element. Of course, more than one element may be associated with the vapor retention assembly and elements of different types may be combined to provide the desired characteristics in terms of water retention and retention of the selected respiratory promoter. For example, a particular vapor retention assembly formed in accordance with the present invention may comprise two fluorophilic exchange elements and a single hygroscopic element. Finally, the volumetric configuration of the vapor retention assembly is not critical and may be selected to optimize the exchange mechanism, reduce dead space volume or lower any pressure drop across the assembly.

Figure 4:
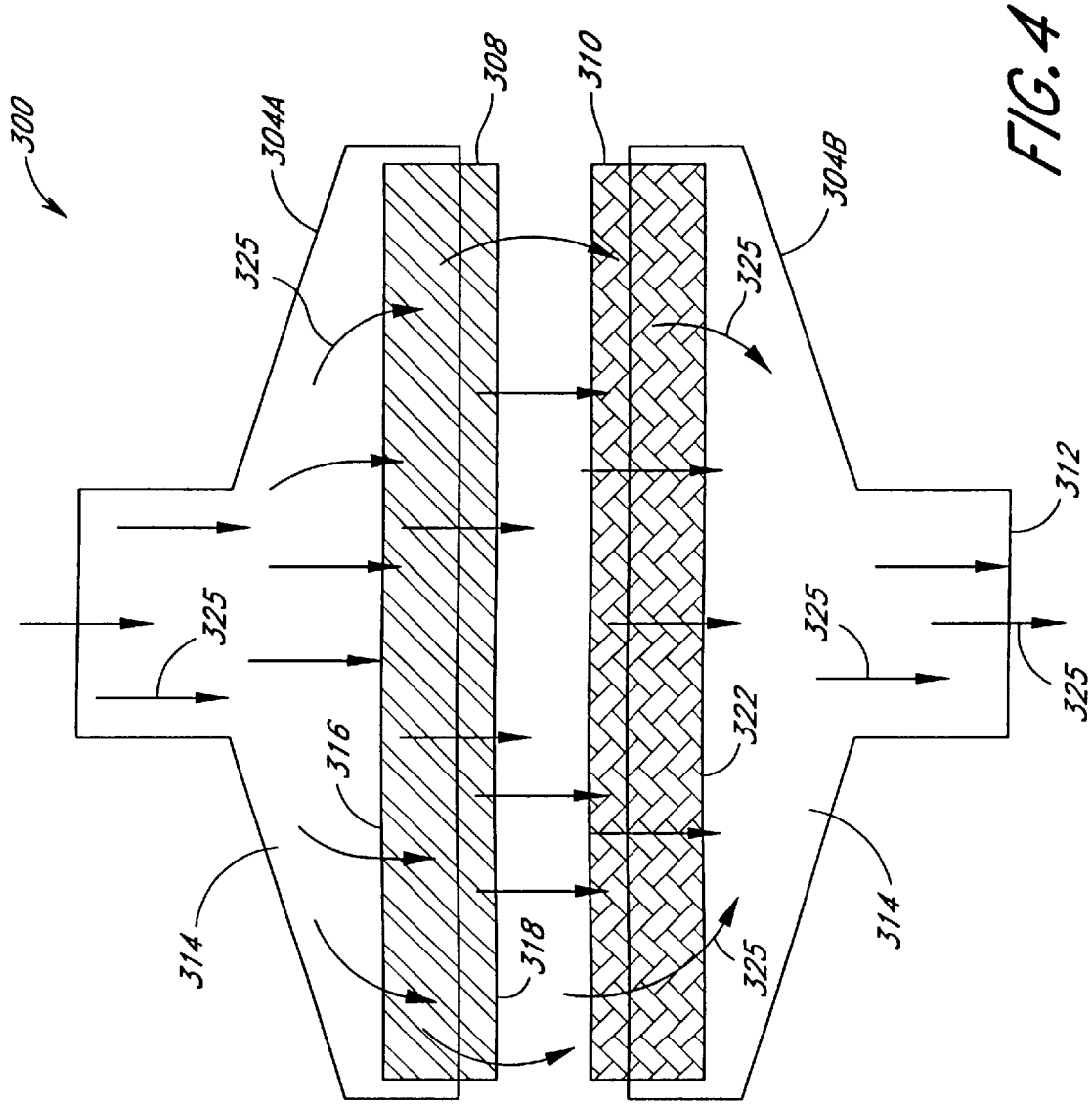
FIG. 4 is an exploded cross-sectional view of a vapor retention assembly comprising a fluorophilic exchange element in accordance with the present invention.

An exemplary embodiment of the present invention comprising a vapor retention assembly is shown in FIG. 4 as an exploded schematic view. The illustrated embodiment could correspond to vapor retention assemblies 160 and 260 shown in FIGS. 2 and 3 respectively. More specifically, vapor retention assembly 300 comprises housing 304, shown here in an exploded configuration, made up of distal housing component 304A and proximal housing component 304B. During use, components 304A and 304B will be sealingly connected to provide housing 304 which defines chamber 314. When sealingly connected, housing 304 and connecting ports 302 and 312 define a gas flow passage that allows a gas to be introduced and removed from chamber 314. When positioned in a ventilation system as shown in FIGS. 2 and 3, connecting port 302 is positioned distally with respect to the patient while connecting port 312 is positioned proximally, vapor retention assembly 300 additionally comprises fluorophilic exchange element 310 having exterior surfaces 320 and 322 as well as hydrophilic exchange element 308 comprising exterior surfaces 316 and 318. During use fluorophilic exchange element 310 and hydrophilic exchange element may be juxtaposed with exterior surfaces 318 and 320 adjacent to each other.

In the embodiment illustrated in FIG. 4 arrows 325 depict the progress of breathing gas through the gas flow passage defined by chamber 314 and connector ports 302 and 304. As connector port 302 is distal with respect to the patient, the illustrated embodiment shows the passage of breathing gas through vapor retention assembly 300 during the inspiratory phase of the respiratory cycle. During the preceding expiratory phase, exhaled gas from the patient comprising vaporized respiratory promoter passed from connector port 312 through chamber 314 and exited connector port 302. As the exhaled gas contacted fluorophilic exchange element 310 at least a portion of the vaporized respiratory promoter was reversibly associated and deposited. Similarly, water vapor was taken up by hydrophilic exchange element 308. Those skilled in the art will appreciate that hydrophilic exchange element 308 also associated with some amount of vaporized respiratory promoter. The exhaled gas, to some extent depleted of both respiratory promoter and water vapor then passed through connector port 302 and, after transport through the expiratory portion of the ventilating system, was vented into the environment or recovered as previously described.

Traveling in the opposite direction of the exhaled gas, the breathing gas entering connector port 302, preferably pressurized by a mechanical ventilator (not shown), is typically at ambient room temperature or warmed slightly and does not contain vaporized respiratory promoter. Upon introduction to chamber 314 the breathing gas contacts exterior surface 316 of hydrophilic element 308. The relative lack of moisture and the thermodynamic conditions of the immediate environment cause water previously associated with hydrophilic element 308 to vaporize and associate with the breathing gas. Further, some portion of the respiratory promoter associated with hydrophilic exchange element 308 is also entrained by the breathing gas. Those skilled in the art will appreciate that the terms vaporized and entrained, whether being used in conjunction with a respiratory promoter or moisture, are being employed in their broadest sense and simply refer the diffusion of a compound in a gaseous medium. That is, the terms may refer to any mist, fume, aerosol, suspension, gas, microparticulates or microdroplets dispersed, and capable of being transported in, a gaseous medium. Typically, but not always, a compound is volatile under physiological conditions. As the gaseous medium is transported by applied pressures, the vaporized or entrained compounds are carried along.

In the instant case the breathing gas, now humidified by contact with hydrophilic exchange element 308 moves toward connector port 312 as shown by arrows 325. The movement of the breathing gas through the gas flow passage is maintained either by the inhalation of the patient, pressure from an attached ventilator or some combination thereof. In any event, after passing from hydrophilic exchange element exterior surface 318 the breathing or inspiratory gas contacts fluorophilic exchange element 310 which intersects the defined gas flow passage. More particularly, in the illustrated embodiment the breathing gas passes distal exterior surface 320, and travels through fluorophilic exchange element 310 before leaving through proximal exterior surface 322. As detailed below, fluorophilic exchange element 310 may be formed from any fluorophilic compound using a variety of fabrication techniques. Through contact with fluorophilic exchange element 310 the concentration of respiratory promoter in the breathing gas is increased substantially. Following contact with fluorophilic exchange element 310 the breathing gas, now comprising vaporized respiratory promoter and water, passes from chamber 314 through proximal connecting port 312. Upon leaving vapor retention assembly 300 the vapor enriched breathing gas passes through any proximal ventilating conduit and patient connector (not shown) before entering the pulmonary air passages of the patient.

It will be appreciated by those skilled in the art that many fluorochemicals, including preferred respiratory promoters, are relatively non-reactive. Unlike most substances, fluorophilic materials physically interact or associate with gaseous or vaporous fluorochemical compounds on a molecular level. Consequently, the fluorophilic exchange elements used in the present invention effectively reduce the loss of respiratory promoters due to thermodynamic and molecular interactions that allow for the reversible association of relatively high levels of fluorochemical vapor. More particularly, the fluorochemical entrained in the expiratory gas associates with the exchange element due to a thermodynamic gradient and physical properties of the element material that favor such association. Conversely, upon the introduction of breathing gas devoid of respiratory promoter in the immediate environment of the exchange element, associated fluorochemical is vaporized or entrained in the passing breathing gas. While not limiting the scope of the invention in any way it is believed that the respiratory promoter is forced into the breathing gas primarily due to a favorable concentration gradient.

As previously alluded to the fluorophilic components of the present invention may be formed from a number of different materials. Preferably the materials employed may comprise at least one halogenated compound. In particularly preferred embodiments the halogenated compound is fluorinated and in particularly preferred embodiments may be polytetrafluoroethylene. It will be appreciated that the fluorophilicity of a compound, and hence its compatibility with the teachings herein, may readily be determined using conventional techniques and do not require undue experimentation. For example, the solubility of the fluorinated monomer in the respiratory promoter of interest is a good indication of compatibility. Other indications comprise materials compatibility tables or experiments that demonstrate swelling of the fluorophilic material upon exposure to the respiratory promoter. Weight gain by potential fluorophilic materials (i.e. more than 5%) upon exposure-of samples to promoter vapor also provides some evidence that they may be used in the vapor retainers of the present invention.

Yet another indication is that the wetting angle will be relatively low for effective materials. More particularly, a small amount (i.e. a drop) of the respiratory promoter of interest is deposited on the surface of candidate exchange materials. After allowing the system to equilibrate, the angle of the drop with respect to the surface of the material is determined. The lower the angle the more the drop has spread out and the more affinity the respiratory promoter has for the tested material. In preferred embodiments of the present invention the wetting angle of a compound used in for forming an exchange element will be less than 45 degrees when tested using perfluorooctyl bromide. In particularly preferred embodiments the wetting angle will be less than 35 degrees and even more preferably will be less than 20 degrees. Especially compatible materials will have wetting angles of less than 10 degrees or even 5 degrees. Accordingly, when combined with the teachings of the instant disclosure one skilled in the art could readily determine which materials are useful for fabricating vapor retention assemblies comprising fluorophilic exchange elements.

The following non-limiting examples are offered as being illustrative of the present invention.

EXAMPLE 1

Fabrication of a Silicone-Based Material Suitable for Use as a Fluorophilic Exchange Element In order to demonstrate the feasibility of forming a fluorophilic exchange element in accordance with the teachings of the present invention a silicone support was infused with a fluorinated compound. Specifically, RTV 630 silicone mixture (General Electric, Waterford, N.Y.) comprising a base and an accelerator in a ratio of approximately 10:1 by weight was combined. Two milliliters of perfluorooctyl bromide (Elf Atochem, Paris, France) was added to ten grams of the silicone mix and the entire composition was mixed well and allowed to cure at 50° C. for at least one hour. The perfluorooctyl bromide appeared to diffuse throughout the silicone matrix which hardened to form a relatively thin pliable sheet. Those skilled in the art will appreciate that the composition could have been molded, cut or otherwise configured to fabricate a fluorophilic exchange element of any desired shape.

EXAMPLE 2

Fabrication of a Silicone-Based Material Comprising Fluorinated Particulates Suitable for Use as a Fluorophilic Exchange Element To demonstrate the feasibility of forming a fluorophilic exchange element comprising a solid fluorinated particulate, a silicone sheet was impregnated with polytetrafluoroethylene was formed according to the teachings herein. More particularly, 2.5 grams of polytetrafluoroethylene particulates was added to 5.1 grams of a silicone mixture similar to that described in Example 1. The polytetrafluoroethylene particulates were dispersed evenly throughout the silicone and the mixture was rolled out and cured for 4 hours at 50° C. on a plastic sheet. The resulting silicone sheet was pliable and soft to the touch.

EXAMPLE 3

Fabrication of a Medical Grade Silicone-Based Material Comprising a Fluorinated Compound Suitable for Use as a Fluorophilic Exchange Element To demonstrate the feasibility of forming a fluorophilic exchange element suitable for use in a therapeutic environment, a medical grade silicone-based material was fabricated. Specifically, Medical Grade Silastic MDX4-4210 (Dow Corning Corp., Midland, Mich.) comprising a base and an accelerator in a ratio of approximately 8:1 by weight was combined. One gram of perfluorodecyl bromide ("PFDB) was mixed thoroughly with 10 grams of the silicone mix. The resulting composition was spread on a plastic sheet and cured for approximately four hours at 50° C. The resulting silicone film was transparent and appeared to be uniform and stable for an extended period.

Those skilled in the art will appreciate that different fluorochemical concentrations, support materials and particulate sizes could be used to control the physical characteristics of the fluorophilic exchange element. In fabricating the exchange elements for inclusion in the vapor retention assemblies of the present invention, various support matrices may be used to provide the desired flow characteristics and increase the operable surface area of the element. Specifically, FIG. 5 shows vapor retention assembly 400 comprising a fluorophilic exchange element 412 composed of fibrous material 414. As shown in the magnified portion of fluorophilic exchange element 412 interstitial spaces 416 are defined by fibrous material 414 which may be formed of a fluorophilic material or comprise support matrix coated with a fluorophilic material. For example, a polymeric fibrous support such as nylon could be rendered fluorophilic through deposition of a silicone based material such as that described in Example 2. Moreover, a hydrophilic material (not shown) could optionally be interwoven with fibrous material 414.

Figure 5:
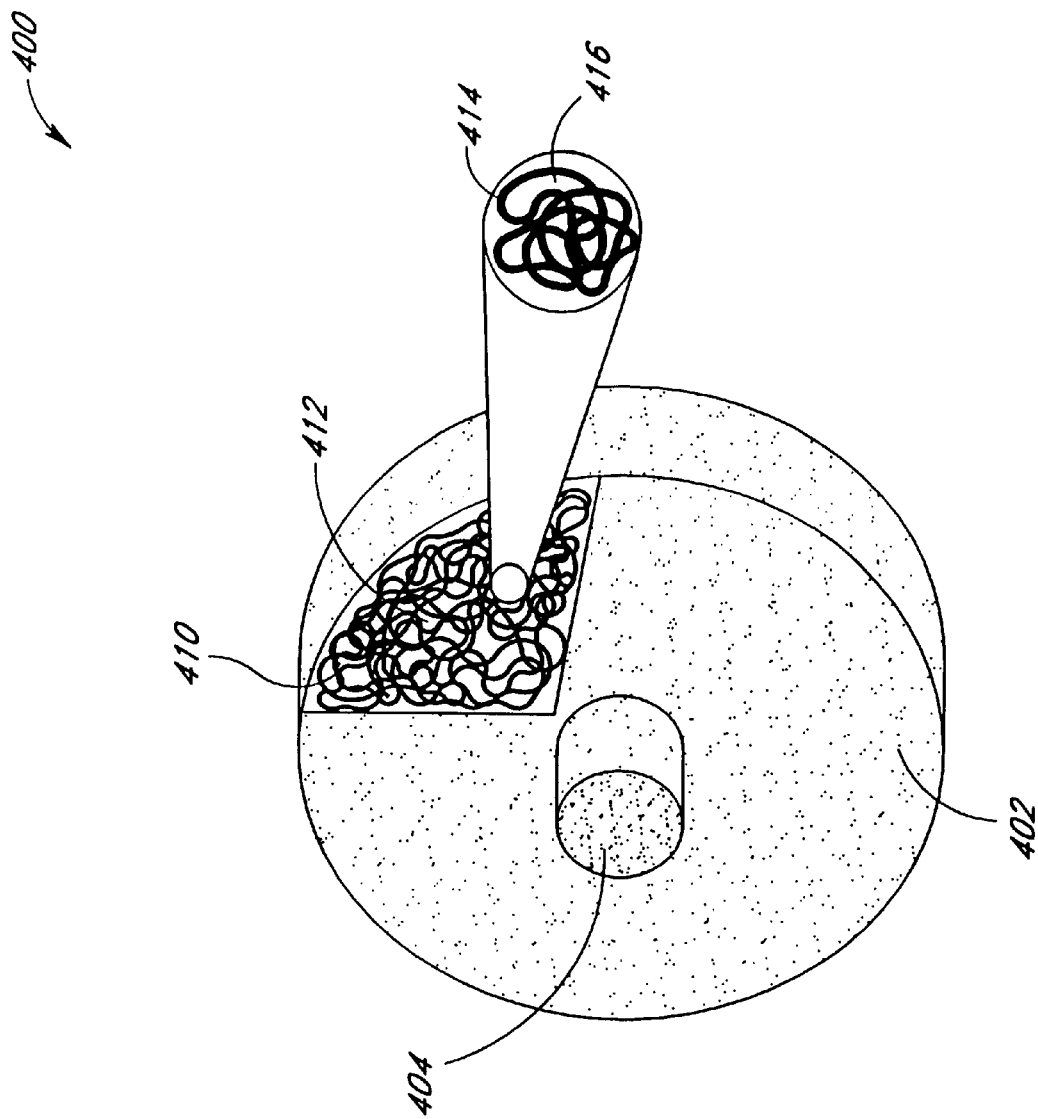
FIG. 5 is a perspective sectional view of a vapor retention assembly comprising a fluorophilic exchange element formed of a foamed material.

In FIG. 5, housing 402 defines chamber 410 and connector port 404. During use either expiratory or inspiratory gas, depending on the orientation of vapor retention assembly 400, would flow through connector port 404 into chamber 410 and contact fluorophilic exchange element 412. Assuming the incoming gas comprised vaporized respiratory promoter, retention of the material would be effected by fluorophilic exchange element 412. More particularly, upon contact with fibrous material 414 the vaporized promoter would become reversibly associated with fluorophilic exchange element through physical or thermodynamically mediated mechanisms. The large surface area and interstitial spaces 416 provided by fibrous material 414 allow for the efficient association and release of the vapor. Upon introduction of a breathing gas comprising oxygen, at least a portion of the deposited vapor will disassociate from fluorophilic exchange element 421 and diffuse in the oxygen containing atmosphere of chamber 410. The respiratory promoter, entrained in the breathing gas, will then be transported to the lungs as the patient inhales.

Preferably, the materials used to fabricate the components of the vapor retention assembly are compatible with any respiratory promoter including breathing liquids. Particularly preferred fabrication materials are generally compatible with fluorochemicals and may be somewhat fluorophilic. Specifically, such materials include, but are not limited to cellulose acetate, polypropylene, polyurethane, polyethylene, polyvinylidene difluoride, stainless steel, Viton®, fluoroelastomers, acrylic, brass, chrome-plated, Cycolac® ABS, polyvinyl chloride, polyvinylidene difluoride, rubber, polycarbonate, polyester, high density polyethylene.

EXAMPLE 4

Fabrication of a Silicone Impregnated Foam Construct for Use as a FluoroDhilic Exchange Element To demonstrate the feasibility of forming a high surface area fluorophilic exchange element a silicone impregnated foam matrix was fabricated. In particular, 6.73 grams of a silicone mixture corresponding to the mixture used in Example 1 was provided. For the purposes of this demonstration no fluorinated compound was included. The free flowing silicone mixture was incorporated into a ½"×4"×4" urethane open cell foam (Keyston Brothers, San Diego, Calif.) by kneading. The silicone mixture appeared to coat all visible surfaces. Following complete impregnation, the silicone coated foam was cured for four hours at 50° C. The resulting construct was pliant and easily deformable. It will be appreciated that a fluorinated compound could be added to the uncured silicone mixture prior to impregnation. As the addition of effective amounts of such fluorinated compounds does not substantially effect the viscosity of the silicone mixture, comparable results would be expected with respect to the final foam construct.

Figure 6:
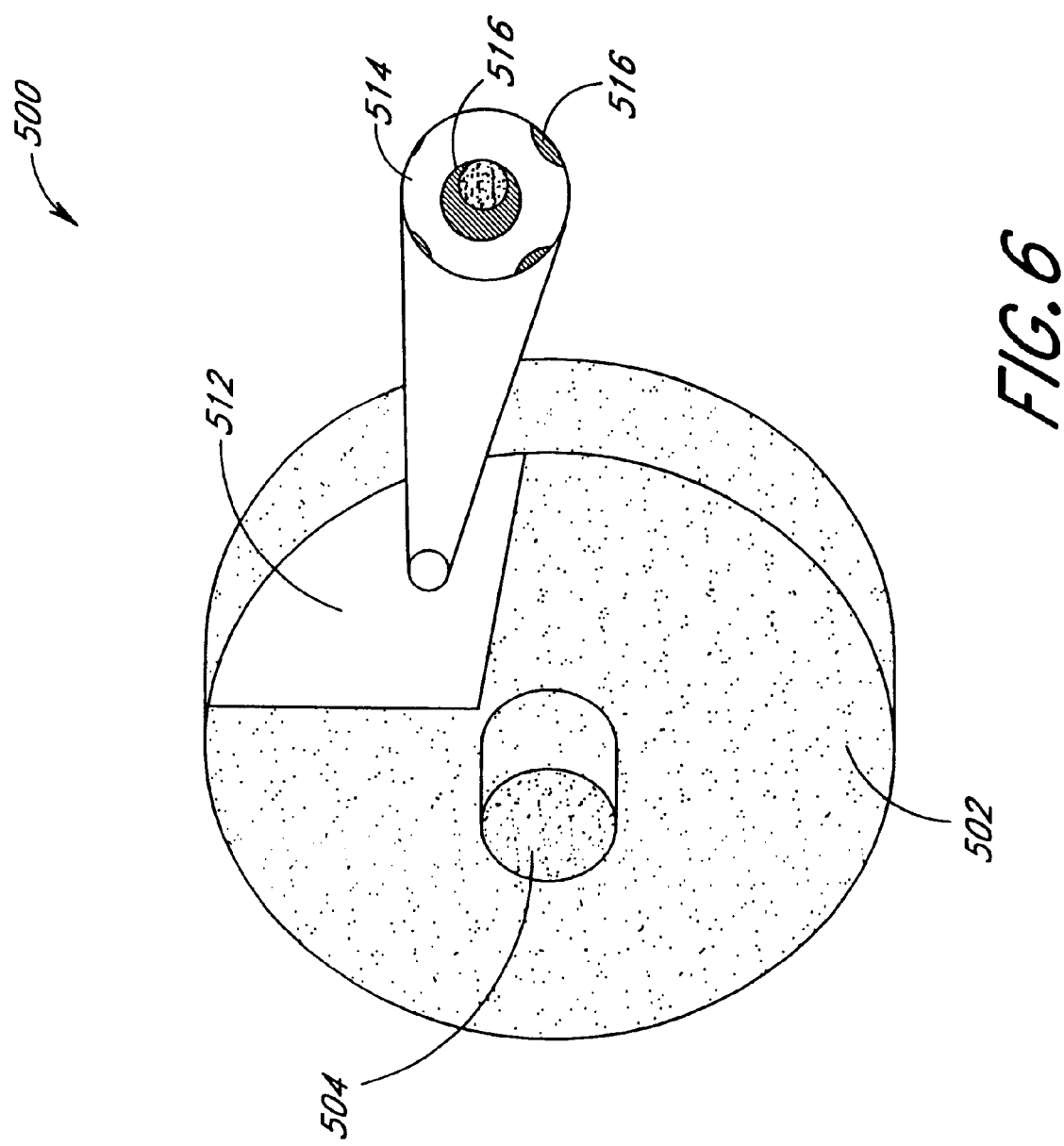
FIG. 6 is a perspective sectional view of a vapor retention assembly comprising a fluorophilic exchange element formed of fibrous material.

A vapor retention assembly comprising a fluorophilic exchange element made according to the preceding example is shown in FIG. 6. More particularly, FIG. 6 shows vapor retention assembly 500 comprising housing 502, connector port 504 and fluorophilic exchange element 512. It will be appreciated that the exchange and retention of respiratory promoter in the lungs is effected substantially the same way as described in relation to FIG. 5. Yet, unlike the vapor retention assembly shown in FIG. 5, fluorophilic exchange element 512 comprises a foam matrix coated with a fluorophilic material. Although the coating material may be selected from any one of a number of fluorinated or non-fluorinated compositions, in selected embodiments the coating material may be silicone. Preferably, the foam support structure is free breathing and incorporates a large number of voids. As shown in the Figure, fluorophilic exchange element 512 comprises coated foam support 514 having a plurality of voids 516. Those skilled in the art will appreciate that almost any void containing structure, including non-foams, are suitable for use in the invention. In the embodiment shown, the inclusion of voids 516 substantially increases the surface area of fluorophilic exchange element 512 thereby increasing the exchange efficiency.

EXAMPLE 5

Fabrication of a Silicone Coated Web Suitable For Use as a Fluorophilic Exchange Element To show the versatility of the present invention, a silicone coated web was fabricated. Specifically, 5.59 grams of a silicone mixture corresponding to the mixture used in Example 1 was provided. For the purposes of this demonstration no fluorinated compound was included. The free flowing silicone mixture was used to coat a 2.5"×17"×0.008" web-like matrix typically used to seal drywall joints. The silicone mixture appeared to coat all visible surfaces. Following transfer of the silicone to the web, the construct was cured for four hours at 50° C. The resulting web was pliant and easily deformable. Those skilled in the art will be appreciated that a fluorinated compound could be added to the uncured silicone mixture prior to impregnation. As the addition of effective amounts of such fluorinated compounds does not substantially effect the viscosity of the silicone mixture, comparable results would be expected with respect to the final web construct.

Figure 7:
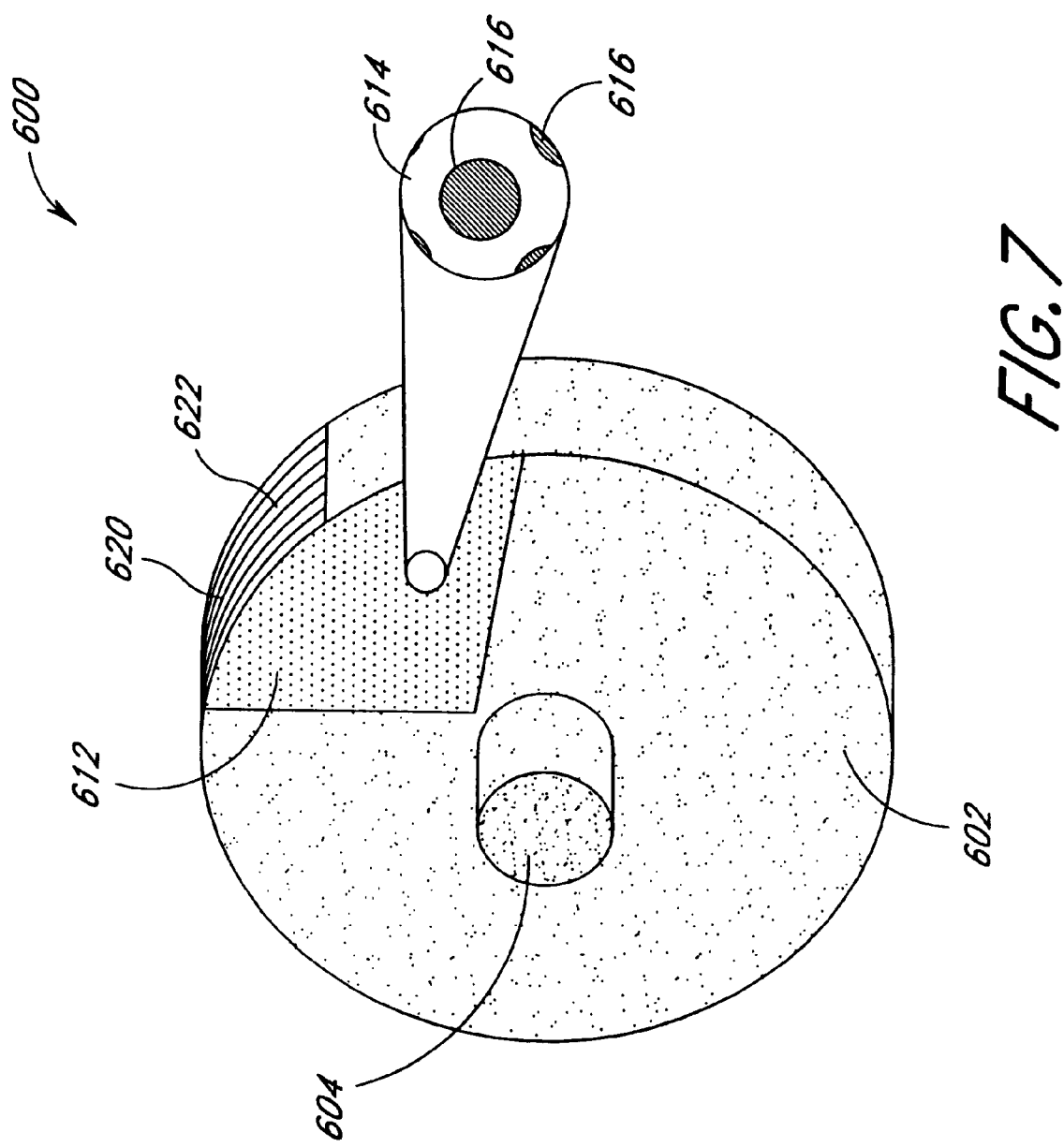
FIG. 7 is a perspective sectional view of a vapor retention assembly comprising a fluorophilic exchange element formed of layers of perforated material.

An exemplary embodiment of a vapor retention assembly formed in accordance with Example 5 is shown in FIG. 7. Specifically, FIG. 7 shows vapor retention assembly 600 comprising housing 602, connector port 604 and fluorophilic exchange element 612. In this embodiment, fluorophilic exchange element 612 comprises a multi-layer structure formed of a series of fluorophilic wafers or disks 620 interleaved with hydrophilic elements 622. As with the previously discussed fluorophilic exchange elements, the individual wafers may comprise a relatively non-active support matrix coated with a fluorophilic material or directly incorporate a fluorophilic compound. In order to increase the surface area of fluorophilic exchange element 612 each of the individual plys is perforated. As illustrated in the magnified surface of fluorophilic exchange element 612, wafers 620 each comprise support matrix 614 having perforations or voids 616 dispersed over the entire surface. Similar to the previously discussed embodiments, voids 616 is substantially increase the overall exchange efficiency of vapor retention assembly 600. Further it will be appreciated by those skilled in the art that the inclusion of hydrophilic exchange elements 622 reduces the need for active humidification of the patient.

EXAMPLE 6

Demonstration of Vaporous Fluorochemical Association with a Fluorophilic Polytetrafluoroethylene Tape In order to demonstrate the fluorochemical associative properties of materials suitable for use as a fluorophilic exchange element, polytetrafluoroethylene tape was suspended in a fluorochemical saturated atmosphere. More particularly, polytetrafluoroethylene tape of the type commonly used for plumbing repairs was cut into strips approximately six inches long and weighed. The tape strips were then rolled up and suspended in a sealed vial containing approximately five milliliters of perfluorooctyl bromide. The vials had been prepared prior to the initiation of the experiment allowing the environment in the vials to equilibrate at room temperature. The tape rolls were suspended above the level of the liquid fluorochemical.

Three vials were prepared and the weight of the individual tape rolls was measured at 0 hours, 6 hours and 72 hours after exposure to the saturated environment. The results of the experiment, with all weights reported in grams, are provided in Table 1 immediately below:

TABLE 1

| SAMPLE: | A | B | C |
|---|---|---|---|
| INITIAL WEIGHT: | 0.2181 | 0.1981 | 0.2074 |
| EXPOSED 6 HOURS: | 0.2504 | 0.2420 | 0.2409 |
| (Percent Increase) | (12.9%) | (18.1%) | (13.9%) |
| EXPOSED 72 HOURS: | 0.3349 | 0.3164 | 0.3127 |
| (Percent Increase) | (34.9%) | (37.4%) | (33.7%) |

A review of the data shows that the suspended polytetrafluoroethylene tape effectively associated with the PFOB vapor in the vial. Specifically, the tape rolls picked up an average of 15% their own weight in PFOB after six hours and an average of 35.3% after seventy two hours. This clearly demonstrates the potential effectiveness of fluorophilic exchange elements with respect to associating fluorochemical vapor.

Figure 8:
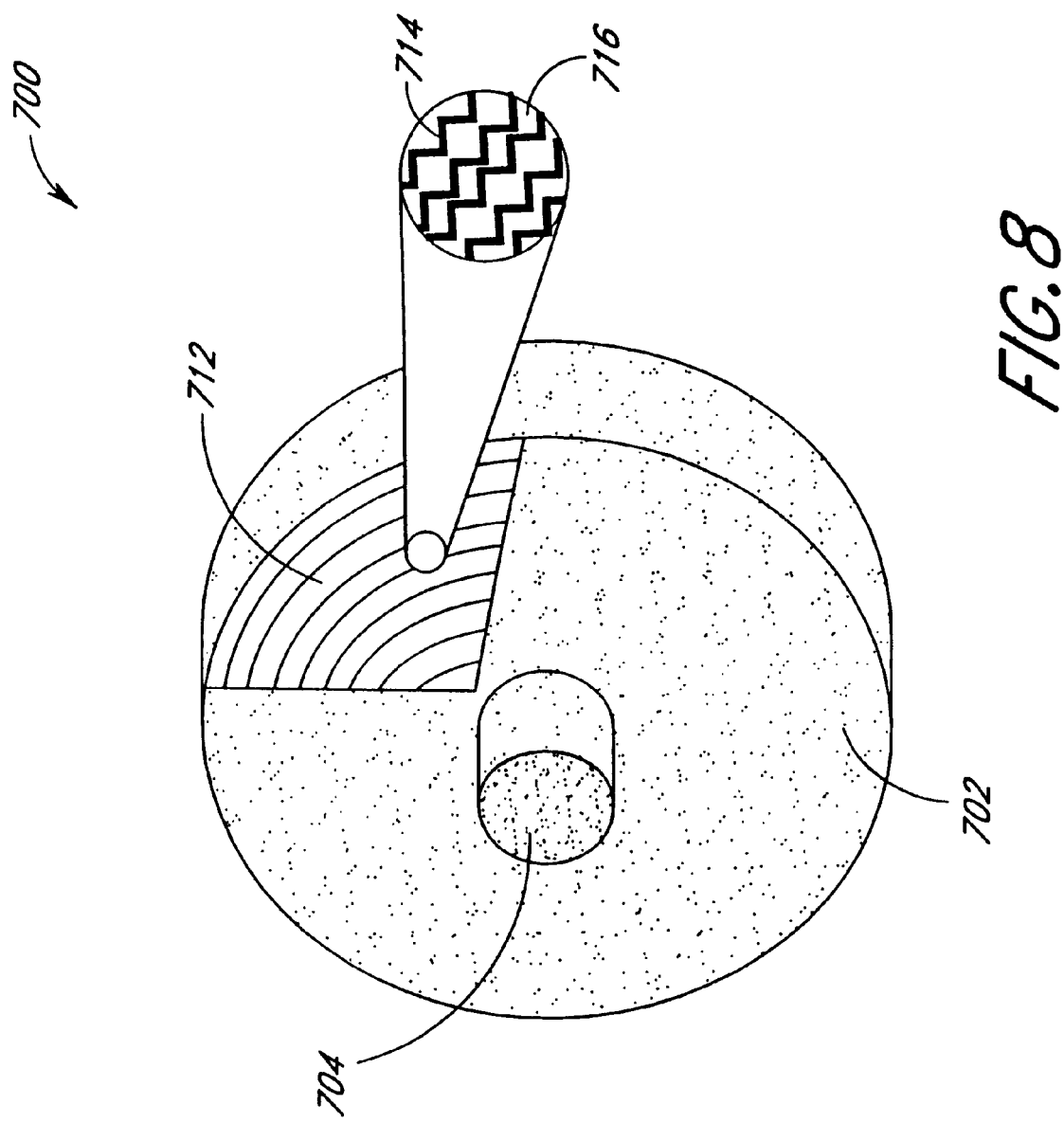
FIG. 8 is a perspective sectional view of a vapor retention assembly comprising a fluorophilic exchange element formed of scrimmed radially rolled tape.

Tape rolls as described in Example 6 may be used to form effective fluorophilic exchange elements in accordance with the present invention. As may be seen in FIG. 8, radially wound fluorophilic tape, preferably comprising polytetrafluoroethylene, provides a relatively cheap way to fabricate the vapor retention assemblies of the present invention. In particular, FIG. 8 shows a vapor retention assembly 700 comprising housing 702, connector port 704 and fluorophilic exchange element 712. Vapor exchange occurs substantially as described with respect to FIG. 5. However, in the instantly illustrated embodiment, fluorophilic exchange element 712, comprises a radially wound fluorophilic tape 714. As detailed in the magnified portion of the Figure, fluorophilic tape 714 is preferably scrimmed and relatively loosely wound to provide interstitial spaces 716. Such a configuration substantially increases the surface area of fluorophilic exchange element 712 and enhances the association and release of vapor. It will further be appreciated that a hydrophilic exchange element (not shown) may be wound radially with the tape to provide pulmonary moisture retention. Additionally, different widths of tape may be employed to optimize the conservation characteristics of vapor retention assembly 700. Similarly, tapes of different composition may be employed.

EXAMPLE 7

Demonstration of Vaporous Fluorochemical Association with a Fluorophilic Polytetrafluoroethylene Fiber To show the applicability of various forms of fluorophilic material in accordance with the present invention, Example 6 was repeated using expanded polytetrafluoroethylene fiber. Specifically, polytetrafluoroethylene fiber (#20346, W. L. Gore and Associates, Elkton, Md.) and polytetrafluoroethylene fiber associated with blended felt (#20347, W. L. Gore and Associates, Elkton, Md.) was cut into sections and weighed. The individual fiber sections were then exposed to PFOB according to the protocol detailed in Example 6. After twenty nine hours of exposure to the fluorochemical vapor the sections were again weighed. The results of the experiment, with all weights reported in grams, are provided in Table 2 immediately below:

TABLE 2

| SAMPLE: | Fiber | Fiber/Felt |
|---|---|---|
| INITIAL WEIGHT: | 0.1934 | 0.1419 |
| EXPOSED 29 HOURS: | 0.2285 | 0.1511 |
| (Percent Increase) | (15.36%) | (6.09%) |

The data collected in this experiment illustrates that polytetrafluoroethylene fibers may be used to form effective fluorophilic exchange elements for use in the present invention. In particular, the fibers may be used to form vapor retention assemblies such as the one shown in FIG. 5. Further, it will be appreciated that the fluorophilic fiber and felt combination will act as a humidifier in addition to reducing the loss of respiratory promoter.

EXAMPLE 8

Evaluation of Various Vapor Retention Assemblies

A total of 11 different vapor retainers were tested to demonstrate the ability of the present invention to reduce the loss of a respiratory promoter from the lungs. The test comprised using the individual vapor retention assemblies for 4 hours of simulated PLV treatment. During that time, evaporation of a fluorochemical from an artificial lung was recorded on a regular basis. For each device and each test, these values were compared to the evaporation of fluorochemical without the vapor retainer in place giving some indication as to the efficiency of the heat and moisture exchanger.

The test circuit consists of an artificial lung or bladder in line with two humidifiers, one filled with perfluorooctyl bromide and the other filled with water, and a standard mechanical ventilator. The vapor retention assembly to be tested is placed between the humidifiers and the ventilator. The humidifiers are operated at relatively high temperatures in order to provide large amounts of perfluorochemical and water evaporation; the temperatures inside average 60° C. for the perfluorochemical and 70° C. in the water filled humidifier. An air cooled heat exchanger is included in-line between the humidifiers and the test device to reduce the gas temperature to physiologic levels. That is, by adjusting the airflow from the fan, the temperature at the test HME is regulated to maintain a constant 34° C. The ventilator (Servo 900c, Seimens Corp.) is operated at a set of conditions which mimic a ventilated adult, and which are included in the ISO 9360 Standard HME Test Procedure.

With each day's testing, a control assembly is tested before and after any runs with actual devices to be tested. The control device is typically a HME of the same configuration as the unit tested with the inner components removed, This configuration is used to simulate the added "dead space" of the HME under test. Calculations for each device under test are compared against that day's control runs.

Most of the heat and moisture exchangers tested are stock units which are already approved for use as moisture exchange devices. Specifically, eight commercially available heat and moisture exchangers were tested along with three vapor retention assemblies, labeled "Experimental" in the table-below, fabricated according to the instant invention. These three assemblies, one comprising a fluoro-silicone exchange element and two comprising ¼" and ½" polytetrafluoroethylene tape respectively, were constructed using housings obtained from commercially available heat and moisture exchangers. The two assemblies comprising tape were of a scrimmed configuration substantially such as that shown in FIG. 5 while the fluoro-silicone assembly was formed by coating a paper filter with fluorinated silicone. Significant features of selected heat and moisture exchangers are indicated in parenthesis next to the model.

TABLE 3

| Device | No. Runs | H$_2$O Efficiency | PFOB Efficiency |
|---|---|---|---|
| Gibeck Humid-Vent 2s (no filter) | 1 × 4 hr. | 40.7% | 13.0 |
| Pall BB50T (electrostatic filter) | 3 × 4 hr. | 47.6 | 21.0 |
| Baxter HCH | 1 × 4 hr. | 70.3 | 31.3 |
| Gibeck Humid-Vent RT30 | 3 × 4 hr. | 56.4 | 33.6 |
| Experimental (fluoro-silicone) | 1 × 4 hr. | 37.0 | 34.0 |
| Mallinckrodt Hygrobac | 3 × 4 hr. | 51.6 | 37.5 |
| 3-M element (no filter) | 1 × 4 hr. | 55.3 | 37.8 |
| Intersurgical Filta-Therm | 1 × 4 hr. | 65.7 | 38.3 |
| Baxter HEPA-HCH | 3 × 4 hr. | 74.7 | 38.6 |
| Experimental (teflon ¼") | 1 × 4 hr. | 51.0 | 40.7 |
| Experimental (teflon ½") | 1 × 4 hr. | 44.7 | 48.7 |

The data shown in Table 3 above demonstrate the applicability of both conventional heat and moisture exchangers and the novel vapor retention assemblies of the present invention for reducing the loss of respiratory promoter from the lung. In this case the tested devices are listed in increasing order of perfluorochemical retention efficiency. Note that while some of the conventional heat and moisture exchangers proved to be effective in retaining fluorochemical, those assemblies comprising a fluorophilic exchange element turned out to be the most efficient. These data clearly demonstrate that the use of either conventional or novel vapor retention assemblies can substantially reduce (by approximately half in some cases) the loss of a respiratory promoter during ventilation therapy thereby cutting costs and increasing the effectiveness of the treatment.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the invention.

What is claimed is:

1. A vapor retention assembly for use in partial liquid ventilation, comprising:

a housing defining a chamber and having a plurality of connecting ports formed therein, said chamber and said connecting ports comprising a gas flow passage through the chamber between the connecting ports, said assembly further comprising a fluorophilic exchange element positioned in said chamber so as to intersect said gas flow passage; and a breathable fluorochemical liquid having a vapor pressure of less than about 75 Torr dispersed in said chamber wherein at least a portion of said breathable liquid is reversibly associated with said fluorophilic exchange element.

2. The vapor retention assembly of claim 1 wherein said fluorophilic element comprises a halogenated material.

3. The vapor retention assembly of claim 1 wherein said fluorophilic exchange element comprises a compound selected from the group consisting of polytetrafluoroethylene, halogenated silicone, fluoroelastomers, polyethylene, polyesters, urethane and combinations thereof.

4. The vapor retention assembly of claim 3 wherein said compound is polytetrafluoroethylene.

5. The vapor retention assembly of claim 1 wherein said fluorophilic exchange element comprises a compound having a wetting angle less than 45 degrees when measured using perfluorooctyl bromide.

6. The vapor retention assembly of claim 1 wherein said fluorophilic exchange element comprises a support material coated with a halogenated compound.

7. The vapor retention assembly of claim 1 further comprising a hygroscopic element or an electrostatic element positioned in said chamber so as to intersect said gas flow passage.

8. The vapor retention assembly of claim 1 wherein said fluorophilic element comprises a substantially flat wafer positioned transversely with respect to said gas flow passage.

9. The vapor retention assembly of claim 1 wherein the breathable fluorochemical liquid comprises a compound selected from the group consisting of perfluorooctyl bromide and perfluorodecalin.

10. The vapor retention assembly of claim 1, wherein said fluorophilic exchange element comprises a fluorocarbon dispersed in a silicone matrix.

11. The vapor retention assembly of claim 10, wherein said matrix is coated onto a support.

12. The vapor retention assembly of claim 1, wherein said fluorocarbon is polytetrafluoroethylene.

13. The vapor retention assembly of claim 1, wherein said matrix is a foam.

14. The vapor retention assembly of claim 13, wherein said foam is urethane.

15. The vapor retention assembly of claim 1, wherein said fluorophilic exchange element comprises polytetrafluoroethylene dispersed in silicone and coated onto urethane foam.

* * * * *